(12) United States Patent
Lopata et al.

(10) Patent No.: US 7,329,542 B2
(45) Date of Patent: Feb. 12, 2008

(54) PROBES FOR IDENTIFYING CANCER-SPECIFIC ANTIGENS

(75) Inventors: Alex Lopata, Richmond (AU); Elza Meeusen, Seddon (AU); Nunzio Mancuso, Glenroy (AU)

(73) Assignee: Cancerprobe Pty Ltd., Victoria (AU)

( * ) Notice: Subject to any disclaimer, the term of this patent is extended or adjusted under 35 U.S.C. 154(b) by 515 days.

(21) Appl. No.: 10/432,906

(22) PCT Filed: Nov. 29, 2001

(86) PCT No.: PCT/AU01/01544

§ 371 (c)(1),
(2), (4) Date: Nov. 24, 2003

(87) PCT Pub. No.: WO02/44216

PCT Pub. Date: Jun. 6, 2002

(65) Prior Publication Data

US 2004/0077841 A1    Apr. 22, 2004

(30) Foreign Application Priority Data

Nov. 29, 2000 (AU) .................................... PR1774

(51) Int. Cl.
 *C12N 5/06* (2006.01)
 *C12N 5/08* (2006.01)
 *G01N 33/48* (2006.01)
(52) U.S. Cl. ........................ 435/372; 435/374; 436/547
(58) Field of Classification Search ..................... None
See application file for complete search history.

(56) References Cited

U.S. PATENT DOCUMENTS

| | | | |
|---|---|---|---|
| 4,855,235 A | | 8/1989 | Takahashi et al. |
| 5,093,261 A | | 3/1992 | Hagiwara et al. |
| 5,650,154 A | | 7/1997 | Theresia Meeusen et al. |
| 5,801,002 A | * | 9/1998 | Raz ........................... 435/7.23 |
| 5,980,896 A | * | 11/1999 | Hellstrom et al. ....... 424/183.1 |
| 6,713,305 B1 | * | 3/2004 | Bachmann et al. ........... 436/64 |

FOREIGN PATENT DOCUMENTS

| | | |
|---|---|---|
| EP | 0 381 427 | 8/1990 |
| WO | WO 00/37503 | 6/2000 |

OTHER PUBLICATIONS abstract of Wheeler (Salud p'ublica de M'exico, (Jul.-Aug. 1997) 39 (4) 283-7).*
Efferson et al (Anticancer Research, 2005, vol. 25, pp. 715-724.*
Bachman et al (Journal of Immunology, 2005, vol. 175, pp. 4677-4685).*
Paul, Fundamental Immunology, (text), 1993, pp. 1157-1170.*
Apostolopoulos et al (Nature Medicine, 1998, vol. 4, pp. 315-320).*
abstract of Semino et al (Journal of Biological Regulators and Homeostatic Agents, 1993, vol. 7, pp. 99-105.*
abstract of Algarra et al International Journal of Clinical and Laboratory Research, 1997, vol. 27, pp. 95-102.*
Bodey et al (Anticancer Research, Jul.-Aug. 2000, vol. 20, pp. 2665-2676).*
Lauritzsen et al (International Journal of Cancer, 1998, vol. 78, pp. 216-222).*
Sarma et al (Journal of Experimental Medicine, 1999, vol. 189, pp. 811-820).*
Ohlen et al (Journal of Immunology, 2001, vol. 166, pp. 2863-2870).*
Antoinia et al (International Immunology, 1995, vol. 7, pp. 715-725).*
Yu and Restifo (Journal of Clinical Investigation, 2002, vol. 110, pp. 289-294.*
Glassy et al, ('Design and Production of Human Monoclonal Antibodies to Human Cancers', In: Human Hybridomas and Monoclonal Antibodies, 1985, pp. 211-225).*
Mukopadhyaya et al (Journal of clinical and Laboratory Immunology, 1989, vol. 30, pp. 21-25).*
Watson et al (Journal of Immunology, 1983, vol. 130, pp. 2442-2447).*
Tureci et al (Hybridoma, 1999, vol. 18, pp. 23-28).*
Olssen et al ('Human—Human Hybridoma Technology', In: Human Hybridomas and Monoclonal Antibodies, 1985).*
Kerr and Thorpe (LabFax, 1994, Table of Contents p. xi).*
Rosenblum et al (Clinical Cancer Research, 1999, vol. 5, pp. 865-874).*
Glassy et al (PNAS, 1983, vol. 80, pp. 6327-6331).*
Yeilding et al (International Journal of Cancer, 1992, vol. 52, pp. 967-973.*
Punt et al (Cancer Immunology Immunotherapy, 1994, vol. 38, pp. 225-232).*
Tokuda et al (British Journal of Cancer, 1999, vol. 81, pp. 1419-1425).*
Alfonso et al., "Generation of Human Monoclonal Antibodies Against Ganglioside Antigens . . . ", Acta Oncologica vol. 35, No. 3, pp. 287-295 (1996).
Zhang et al., "v-rel Induces Ectopic Expression of an Adhesion Molecule, . . . ", Molecular and Cellular Biology, Mar. 1995, vol. 15, No. 3, pp. 1806-1816.
Lynch et al., Cancer immunology, Current Opinion in Oncology 1993, 5:145-150.
Fantozzi, "Development of Monoclonal Antibodies With Specificity to Oral Squamous Cell Carcinoma", Laryngoscope 101: Oct. 1991, pp. 1076-1080.
Imam et al., "Characterization of a Cell Surface Molecule Expressed on B-Lymphocytes and Hodgkin's Cells", Cancer Research 50, pp. 1650-1657, Mar. 1, 1990.

(Continued)

*Primary Examiner*—Karen A. Canella
(74) *Attorney, Agent, or Firm*—B. Aaron Schulman; Stites & Harbison PLLC

(57) ABSTRACT

This invention relates to the diagnosis of cancer, and in particular to the identification and detection of cancer-specific antigens, the invention provides antibody probes and methods for using the probes for detection and purification of cancer-specific antigens, and in the preparation of vaccine compositions. Antibodies against cancer-specific antigens are also disclosed and claimed.

13 Claims, 13 Drawing Sheets

OTHER PUBLICATIONS

Larson et al., "Localization of Antibody-Secreting Cells against Human Colon Adenocarcinoma Cell Lines Using the Enzyme-Linked Immunospot Assay", Int. Arch. Allergy Appl. Immunol. 1988; 87:405-408.

Meeusen et al., "Antibody secreting cells as specific probes for antigen identification", Journal of Immunological Methods 172 (1994), pp. 71-76.

Meeusen et al., "The use of antibody-secreting cell probes to reveal tissue-restricted immune responses during injection", Eur. J. Immunol. 1994, 24, pp. 469-474.

Rughetti et al., "Human B-Cell Immune Response to the Polymorphic Epithelial Mucin", Cancer Research 53, Jun. 1, 1993, pp. 2457-2459.

Jehuda-Cohen et al., "Polyclonal B-cell activation reveals antibodies against human immunodeficiency . . . ", Proc. Natl. Acad. Sci., vol. 87, pp. 3972-3976, May 1990.

Kagami et al., Production and Characterization of Monoclonal Antibodies to Fcγ 2a-Binding Protein Isolated From the Detergent . . . , Journal of Leukocyte Biology, 45:311-321 (1989).

* cited by examiner

- Antigens may also be directly bound to the ELISA wells.

PROBES FOR IDENTIFYING CANCER-SPECIFIC ANTIGENS

This invention relates to the diagnosis of cancer, and in particular to the identification and detection of cancer-specific antigens. The invention provides antibody probes and methods for using the probes for detection and purification of cancer-specific antigens, and in the preparation of therapeutic, diagnostic and vaccine compositions, as well as in the preparation of antibodies directed against cancer-specific antigens.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

Considerable effort has been devoted to the search for therapies and diagnostics for cancers. The identification of cancer-specific molecules has remained the major stumbling block to the generation of suitable and effective therapies and diagnostics. One of the major reasons for this is the similarity between cancer cells and normal cells. It is possible that there are only very subtle variations in the proteins encoded during the formation of cancer cells. The search for these subtle variations is often driven by hope or inspiration, and entails considerable difficulty, expense and time.

Lung, colon and breast cancers are among the most common malignant tumours in humans. While methods of treatment have vastly improved in recent years, the effectiveness of treatment is critically dependent on early diagnosis. For example, while 70 to 80% of early detected, lymph node-negative breast cancer patients survive over 10 years after primary therapy, more than 60% die in this period if the tumour cells have already reached the lymph nodes before the commencement of treatment. The most efficient methods of early diagnosis for breast cancer are self-examination and mammography. No such method of early diagnosis is available for lung cancers, which can only be detected by radiography, which is usually carried out after symptoms become apparent, resulting in a much lower ten-year survival rate (approximately 13%). It is therefore generally accepted that improved, simple methods of early diagnosis would have a profound effect on the outcome of cancer treatments and mortality.

The most commonly used technique in clinical diagnosis in both veterinary and human medicine is the detection of antibodies or antigens in the serum of patients. The usefulness of serological tests for cancer diagnosis has however been disappointing, partly because cancer-specific or cancer-associated antigens have not been well defined and characterised. In addition, the use of serum as a source of specific antibodies has several inherent disadvantages, including:

1. The presence of large amounts of serum antibodies not related to the pathological agent, resulting in false positive results and background reactions;
2. The formation of antigen-antibody complexes in the serum which can disguise the presence of low titre antibodies/antigens;
3. The inability to detect antibodies produced locally at restricted mucosal sites, such as breast, colon and lung tissues, in the serum because of the massive dilution of these antibodies upon movement into the blood; and
4. The likelihood of persistence of specific antibodies in the serum, even in the absence of current disease makes it difficult to differentiate between previous and current disease.

Prior art methods have primarily been directed to generation of monoclonal antibodies directed to cancer-specific antigens. For example, U.S. Pat. No. 5,093,261 by Hagiwara et al. discloses the generation of human hybridoma cell lines which produce monoclonal antibody specific for a primary liver cancer by fusion of lymph node lymphocytes from a patient with liver cancer with cells of a lymphoblastoid cell line. However, such methods are directed to making monoclonal antibodies against an unidentified antigen of a known cancer, rather than to identifying a cancer-specific antigen. In addition, monoclonal antibody production requires complex in vitro fusion and selection proceedings; the monoclonal antibodies thus produced do not reflect the total polyclonal immune response mounted against the cancer by the B cells in the draining lymph nodes. There is no disclosure or suggestion that the methods disclosed therein could be applied to preclinical diagnosis, staging of cancers, or detection of metastasis.

Therefore it was an objective of the inventors to develop methods for identifying antigenic molecules, or parts thereof, which are specific for individual cancers. Such molecules would be useful in the development of diagnostic or therapeutic agents for specific cancers.

We have previously shown that it is possible to identify protective antigens which are specific for pathogens such as parasites or bacteria of veterinary importance by culturing antibody-secreting cells from draining lymph nodes adjacent to a site of infection, isolating immunoglobulins from the culture medium, and using these immunoglobulins to identify pathogen-specific antigens. See for example U.S. Pat. No. 5,650,154; Meeusen and Brandon 1994a,b; and Walker et al, 1994, the entire disclosures of which are incorporated herein by this reference.

This method, which we have designated "ASC-probe technology", utilises antibody-secreting cells as the source of the antibodies, and has been used extensively and successfully in the identification of new stage-specific and tissue-specific antigens and antibodies in endo- and ectoparasite, bacterial and mycoplasmal infections (Meeusen and Brandon 1994a, b; Walker et al, 1994; Walker et al, 1996; Bowles et al, 1995; Bowles et al, 1996). This method also makes use of the versatility of antibodies to identify and detect antigens by commonly used methods, such as Western blotting and immunoprecipitation. The source of the antibodies is not serum but antibody-secreting cells (ASC). It has long been established that ASCs are induced in the local lymph nodes draining a disease-affected tissue, where antigen is deposited. From the lymph nodes, activated lymphocytes, including ASCS, migrate via the efferent lymphatic vessel through the bloodstream to the target tissue. The ASCs within the lymph nodes are short-lived, surviving for 4-6 days, and are only present as long as the antigenic stimulus is present within the tissue.

In addition, we have shown that the specific ASCs are restricted to the lymph nodes draining the affected organ or tissue, and that different lymph nodes within the same animal can react independently to different stages of infection with a pathogen, generally with different isotype and antigen recognition profiles (Meeusen and Brandon 1994b).

When cultured in vitro, the ASCs isolated from infected tissue or draining lymph nodes can be induced to secrete high levels of specific antibodies into the culture supernatant for several days. The antibody-containing supernatant, which we refer to as "ASC-probes", is used directly to detect the presence and variety of antigens present at a particular time and tissue site and stage of infection. In addition to preparing ASC-probes from infected tissues and draining lymph nodes, we have also been able to isolate specific ASC-probes from circulating blood by making use of the narrow window of opportunity when ASCs are migrating from the lymph nodes to the tissue via the blood circulation. We have found that ASC-probes have distinct advantages over the use of serum antibodies for the discovery of novel pathogen-specific antigens useful for diagnosis and vaccine development.

In addition, the use of ASC-probes overcomes the major disadvantages of using serum antibodies mentioned above, in that:

1. ASCs are only generated after antigen stimulation, and the antibodies present in the ASC-probes are therefore predominantly specific for the disease agent, significantly reducing background and non-specific reactions;

2. As the cells used for ASC-probe preparation are washed free of serum before culture, there is no antigen present, and no antigen-antibody reaction which can reduce the sensitivity of the assay can occur;

3. ASCs locally produced in mucosal tissues can be isolated from tissue or from lymph nodes, or from peripheral blood during their migration to tissues;

4. As ASCs in lymph nodes are short-lived, they are only present as long as the antigenic stimulus is present in the tissue; the production of ASC-probes therefore reflects current infection or disease; and 5. ASC-probes, including those present in or secreted by peripheral blood lymphocytes, can provide a positive diagnosis, even at a stage when circulating antibody cannot be detected.

Since the development of this technique, there has been one publication reporting the use of peripheral blood ASCs for the detection of HIV infection in seronegative patients (Jehuda-Cohen et al. 1990).

While the use of ASC-probes has proven to be a major breakthrough in research relating to vaccines against infectious diseases(Meeusen and Maddox, 1999), this technique has not yet been applied to cancer research. The pathogenesis of cancers is very different from that of parasitic or bacterial infections, and cancer-specific protective responses are primarily T cell rather than B cell responses. Several studies have however reported the presence of activated B cells and plasma cells within draining lymph nodes and infiltrating lymphocytes of breast cancers (see for example Lynch and Houghton, 1993). However, there is no evidence as to whether this represents a specific response to a cancer-associated antigen, and the nature of these antigens has not been identified. Despite this, we believed that it was possible that cancer antigens might be specifically recognised by lymphocytes from adjacent lymphoid tissues. We therefore wished to determine whether the ASC-probe approach could also be successfully applied to cancer research, and whether ASC-probes could be used for the detection of novel tissue-specific and cancer-associated antigens, and for the early diagnosis of primary or recurrent cancer.

SUMMARY OF THE INVENTION

In a first aspect, the invention provides a method for producing an antibody-secreting cell probe (ASC-probe) against a cancer-specific antigen, comprising the steps of:

(a) obtaining a biological sample from an animal suffering from a cancer;

(b) isolating a population of cells from the biological sample;

(c) culturing the cells in vitro in a suitable culture medium; and (d) harvesting antibodies produced by lymphoid cells present in the cell population.

The cancer may be a solid tumour, such as a cancer of the breast, ovary, uterus, prostate, colon, or lung, or a lymphoma, or may be a leukemia.

The cancer specific antigen may be a polypeptide or peptide, a glycoprotein, an oligosaccharide, a polysaccharide, or a glycolipid. However, it will be appreciated that this does not exclude the possibility that the antigen may have some other chemical structure. All that is required is that the antigen is capable of eliciting antibody production.

It will be clearly understood that the ASC probe may be of any antibody isotype. In particular, while in many cases the ASC probe will be an IgG, the invention specifically encompasses ASC-probes which are IgA.

The animal from which the biological sample is taken may be a mammal, including humans. The term mammal includes companion animals such as dogs and cats, and domestic animals such as horses, cattle and sheep, or zoo animals such as felids, canids, bovids, and ungulates.

The biological sample may be of any suitable type, for example spleen, blood, lymph or lymph node, or bone marrow, but is preferably from a tissue area which is rich in lymphoid cells and is close to the site of the cancer, such as a draining lymph node. In the case of leukemias, the biological sample is preferably spleen or bone marrow.

In general blood samples are not preferred, because it has been found that the majority of antibodies found in a serum or plasma sample are irrelevant to the cancer. In addition, serum or plasma components may interfere with the specific reactions between cancer antigens and the corresponding antibodies. In contrast, the ASC-probes of the invention are highly enriched in cancer-specific antibodies. However, it will be appreciated that for some conditions such as leukemias it may be necessary to use blood as a source of antibody-secreting cells.

The cells isolated from the biological sample preferably include B lymphocytes and/or B memory cells. Optionally the sample is subjected to one or more processes for enrichment of lymphocytes or B lymphocytes. Suitable processes for such enrichment are well known in the art; see for example Goding, 1986. Cell populations which may suppress antibody secretion, in particular $CD8^+$ T cells, may optionally be selectively depleted, for example by complement-mediated lysis of selected cell populations with monoclonal antibodies (mAbs) against CD5, CD8, CD4 and/or γδ-TCR (Kamath et al., 2000).

Because the level of antibody secretion into the culture medium may be very low without in vitro stimulation of resting lymphocytes, the method preferably includes a further step of activating the isolated cells to proliferate and to secrete antibodies, by adding a cell activating agent or a cell proliferation agent to the culture medium. In vitro secretion of antibodies into the culture medium by recently activated B cells may also be enhanced by the addition of mitogens or helper factors to the cultures.

The cell activating agent is preferably selected from the group consisting of mitogens and helper factors produced by leukocytes, their synthetic equivalents, or combinations thereof.

The mitogen is preferably selected from the group consisting of pokeweed mitogen (PWM), polyvinylpyrrolidone (PVP), phytohemagglutinin (PHA), Concanavalin A (Con A), CD40 ligands (see Banchereau et al., 1994) polyadenylic-polyuridylic acid (poly(A-U)), purified protein derivate (PPD), polyinosinic-polycytidylic acid (poly(I-C), lipopolysaccharide (LPS), staphylococcal organisms or products thereof, Bacto-streptolysin O reagent (SLO), staphylococcal phage lysate (SPL), Epstein-Barr virus (EBV), Nocardia water-soluble mitogen (NWEM), and dextran sulphate, or is a mixture of two or more of these agents.

The cell proliferation agent may be any agent which indirectly or directly results in B cell proliferation and/or antibody secretion, such as solid-phase anti-immunoglobulin.

The helper factor may be a cytokine, such as an interleukin, a colony stimulating factor, an interferon, or any other helper factor which has been shown to have a stimulatory effect on specific B cell proliferation and/or antibody secretion, either alone, or in combination with other factors and agents. Interleukin 6 is preferred.

It will be appreciated that cell activating agents, cell proliferation agents, mitogens or helper factors may be used separately or in combination, and that one or more of each of the additives may be used.

The ASC-probes are suitably harvested by separating the supernatant from the cells by centrifugation. The supernatant contains antibodies secreted by the cells during culture, or released from the B cells, for example by lysis of the B cells.

In a second aspect, the invention provides an ASC-probe directed against a cancer-specific antigen; preferably the ASC is prepared using the methods of the invention. In one preferred embodiment of this aspect of the invention, the ASC probe is coupled to a solid support, which is preferably one suitable for affinity chromatography, as discussed below. In a second preferred embodiment, the ASC probe is labelled with a detectable marker, such as a radioactive, fluorescent, enzymic, or chemiluminescent label; suitable such labels are well known to those skilled in the art, and the coupling may be performed by conventional methods. Biotin is a particularly preferred label.

The ASC-probes may be utilized simply in the form of the supernatant harvested from the cultured cells. Alternatively, the antibodies may be separated and purified. The ASC-probes can be purified by conventional methods used to purify immunoglobulins from serum or plasma or from tissue culture medium, such as precipitation with ammonium sulphate, fractionation with caprylic acid, ion exchange chromatography, or binding to and elution from immobilized anti-immunoglobulin, protein G or protein A.

Accordingly, in a third aspect the invention provides a method of isolating an antigen associated with a cancer, comprising the steps of:

(a) obtaining a tissue or cell sample from a cancer;

(b) reacting the sample with an ASC-probe according to the invention, thereby to detect at least one antigen; and (c) isolating the antigen thus detected.

It will be appreciated that the cancer-associated antigen may be specific to a particular cancer, or alternatively may not be specific, but may nevertheless be useful in diagnosis and/or treatment of the cancer.

The cell or tissue sample may suitably be mixed with a standard buffer solution and placed on a standard support such as an SDS-polyacrylamide gel to separate the proteins present therein by electrophoresis. The separated proteins may then be transferred to nitro-cellulose, nylon or other sheets.

The step of reaction with an ASC-probe preferably further includes detecting the product thus produced, using a detection assay such as Western blotting, immunoprecipitation assay, a radioimmunoassay, an enzyme-linked immunoassay, chemiluminescent assay or immunofluorescent assay.

The ASC-probe of the invention may be used for the affinity purification of a cancer-specific antigen. Thus in a third aspect the invention provides a method for purifying a cancer-specific antigen, comprising the steps of:

(a) subjecting a crude antigen mixture present in an extract of cancer cells or cancer tissue to affinity chromatography using an ASC-probe according to the invention, immobilized on a suitable support, and (b) isolating antigen bound to the immobilised ASC-probe.

The ASC-probe of the invention can be immobilised by coupling it to any suitable solid support, e.g. CNBr-activated Sepharose 4B (Pharmacia), Affi-gel (Bio-RAD) or other affinity chromatography supports able to bind proteins, using the methods recommended by the manufacturer. The immobilized ASC-probe can then be used for the fractionation and purification of specific antigen from a complex dell or tissue extract by affinity chromatography. After binding of antigen to immobilized ASC-probe, unbound or loosely bound macromolecular species can be washed away from the solid support with a buffer, for example a buffer containing 1.5M NaCl. Subsequently the antigen can be eluted from the affinity column with low or high pH buffer or a buffer containing chaotropic ions, such as 0.5-3.0M sodium thiocyanate.

The application of the ASC-probe of the invention to affinity chromatography enables sufficient quantities of cancer-specific antigens to be rapidly isolated from a complex crude extraction mixture for biochemical characterization, amino-acid sequencing and investigation of the ability of the antigens to elicit a protective immune response. The use of affinity chromatography for obtaining antigen(s) avoids the difficulties often encountered when applying conventional biochemical techniques to the purification of an antigen about which little or no data is known. It also obviates the need to raise polyclonal or monoclonal antibodies for the purpose of analytical affinity chromatography. Large-scale preparation may, however, require the preparation of polyclonal or monoclonal antibodies.

Having thus identified a cancer-specific antigen, where the antigen is a polypeptide or peptide, conventional molecular biology techniques such as cloning, or chemical techniques such as solid phase polypeptide synthesis may be used to produce large amounts of the antigen. Peptides corresponding to different epitopes of the antigens may be used to produce a vaccine. It will be clearly understood that the cancer-specific antigen may also be a glycoprotein or an oligosaccharide, a polysaccharide, a glycolipid, or some other chemical structure.

Accordingly in a fifth aspect the invention provides a method for preparing a cancer-specific polypeptide or peptide antigen, comprising the steps of:

(a) providing a DNA library derived from a sample of a cancer;

(b) generating polypeptides from the library;

(c) probing the polypeptides with an antibody probe selected from the group consisting of an ASC-probe according to the invention, a monoclonal antibody derived therefrom, or a derivative of such a monoclonal antibody;

(d) identifying cDNA or genomic clones which produce polypeptides which react with the antibody probe; or (e) probing the cDNA or genomic library with synthetic oligonucleotide probes based on the amino acid sequence of the antigen identified and purified as described above; and (f) isolating the clones thus detected.

Either a cDNA library or a genomic library may be used. The library may be assembled into suitable expression vectors that will enable transcription and the subsequent expression of the cloned DNA, either in prokaryotic hosts such as bacteria or eukaryotic hosts such as yeast or mammalian cells.

The antibody probes in step (c) are preferably selected from:

(i) antibodies obtained from the culture medium produced as described above;

(ii) monoclonal or polyclonal antibodies produced against an antigen identified and purified as described above;

(iii) recombinant or synthetic monoclonal antibodies or polypeptides with specificity for an antigen identified and purified as described above, e.g. antibodies prepared as described by Ward et al (1989); and (iv) single chain antibodies produced against an antigen identified and purified as described above.

It will be clearly understood that the antibodies of (iii)-(v) may be produced using a recombinant antigen according to the invention, or an antibody which has been derived from cDNA extracted from lymphocytes. Methods for the latter are described in U.S. Pat. No. 5,627,052 by Schrader.

In one preferred embodiment the antigen is able to elicit a protective antibody against a cancer. Protective antibodies can be identified by their ability to cause regression of the cancer and/or to delay progression of the cancer, using methods known in the art.

In another preferred embodiment the antigen is associated with a specific stage of development of the cancer. Such stage-specific antigens are useful in diagnostic staging of cancers in individual patients.

In a third preferred embodiment the antigen is able to elicit lymphocyte proliferation and/or production of cytokine by antigen-specific lymphocytes; this may readily be assessed using methods known in the art.

In a sixth aspect the invention provides a polyclonal or monoclonal antibody directed against a cancer-specific antigen according to the invention. Such antibodies may be used in diagnostic tests, or for passive treatment of the cancer. It will be appreciated that polyclonal or monoclonal antibodies and fragments or analogues of monoclonal antibodies, such as ScFv fragments, humanized monoclonal antibodies, bispecific or chimeric antibodies are within the scope of the invention; methods for production of such polyclonal or monoclonal antibodies, fragments or analogues are well known in the art.

In a seventh aspect the invention provides a therapeutic or diagnostic composition, comprising a cancer-specific antigen according to the invention, together with a physiologically or diagnostically acceptable carrier. Where the composition is a diagnostic composition the antigen may be specific to a particular stage of the cancer.

In an eighth aspect the invention provides a composition comprising a therapeutically effective amount of at least one antibody or specific ligand which binds to a cancer-specific antigen identified according to the invention, together with a pharmaceutically acceptable carrier. Preferably the antibody is a monoclonal or recombinant antibody which binds specifically to the antigen. The specific ligand may be a lectin or a peptide selected for specific binding to the antigen, for example by panning of a peptide library. This and other suitable methods of selection are well known in the art.

In a ninth aspect the invention provides a method for the treatment of cancer in an animal, comprising the step of administering a therapeutically effective amount of an antibody or specific ligand to a cancer-specific antigen produced according to methods of the invention to an animal in need of such treatment. Preferably the antibody is a monoclonal antibody. The antibody or ligand may optionally be linked to a toxin such as diphtheria toxin or ricin or to a chemotherapeutic agent, and used to target the toxin or agent to the tumour cells.

In a tenth aspect the invention provides a vaccine composition against a cancer, comprising a prophylactically or therapeutically effective amount of at least one protective antigen prepared by a method of the invention, or an antigenically-active antigen fragment thereof, optionally together with an adjuvant.

The vaccine or composition according to the invention may be administered orally, or may be administered parenterally, for example by intramuscular, subcutaneous or intravenous injection. The amount required will vary with the antigenicity of the active ingredient, and need only be an amount sufficient to induce an immune response typical of existing vaccines, which may readily be determined by routine experimentation. Typical initial doses will be approximately 0.001-1 mg active ingredient/kg body weight. The dose rate may be increased, or multiple doses may be used as needed to provide the desired level of protection.

The vaccine or composition according to the present invention may further include a pharmaceutically acceptable carrier, diluent or excipient therefor. Preferably the active ingredient is suspended or dissolved in a physiologically acceptable carrier. The carrier may be any solid or solvent which is non-toxic to the animal and compatible with the active ingredient. Suitable carriers include liquid carriers, such as normal saline and other non-toxic salts at or near physiological concentrations, and solid carriers, such as talc or sucrose. Adjuvants, such as complete or incomplete Freund's adjuvant, alum, or iscoms, or immunomodulators such as cytokines may optionally be added to enhance the antigenicity of the antigen. When used for administration to the lungs, the vaccine composition is suitably in the form of an aerosol.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

For the purposes of this specification it will be clearly understood that the word "comprising" means "including but not limited to", and that the word "comprises" has a corresponding meaning.

10 µl of biotinylated antibody at 1/150 and 1/500 dilution respectively was loaded on a 10% SDS-PAGE gel, transferred to nitrocellulose, incubated with peroxidase-conjugated streptavidin and developed by enhanced chemiluminescence.

Figure 3:
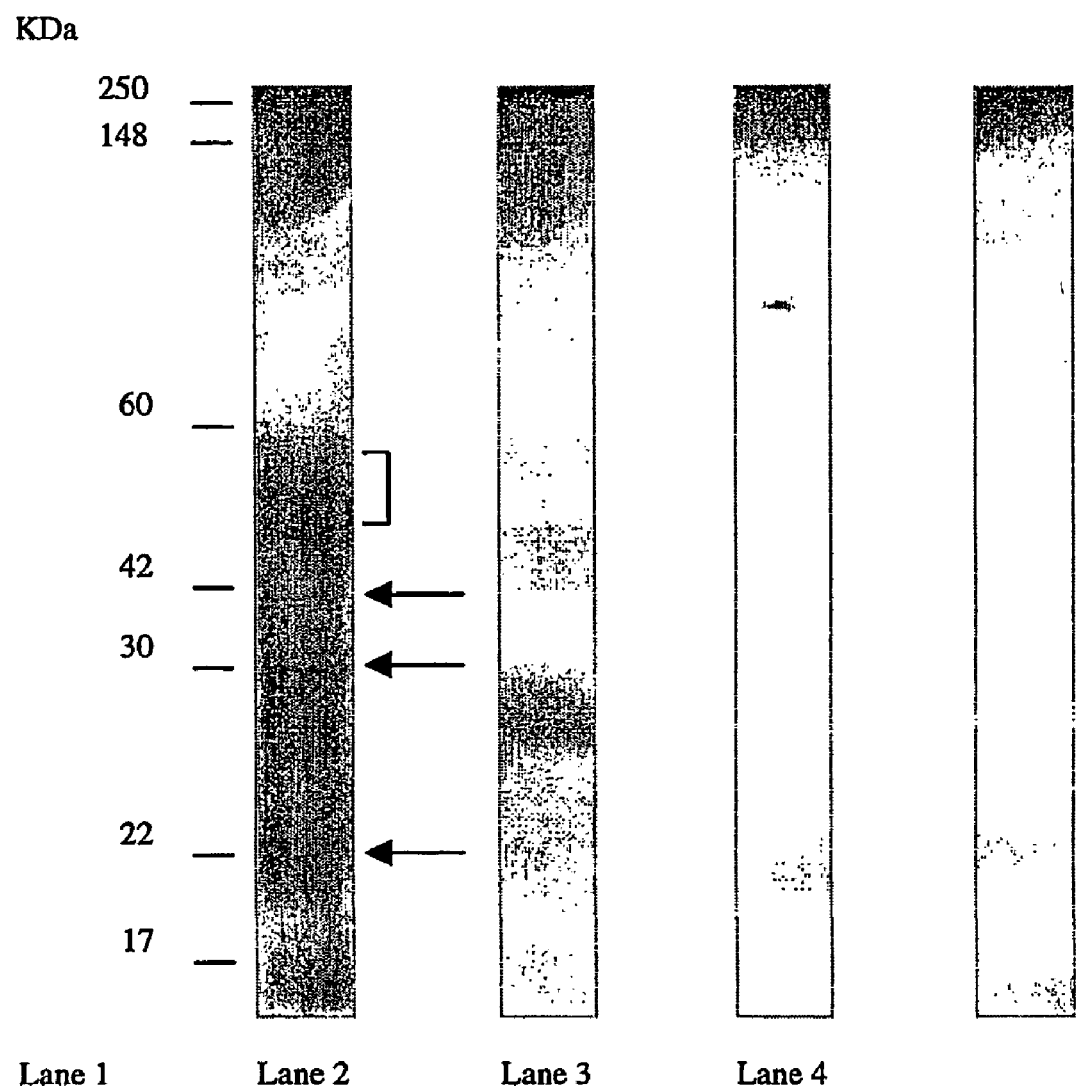

FIG. 3 shows the results obtained with samples from breast cancer patients, using Western blotting on nitrocellulose from a 10% SDS-PAGE gel.

Samples were solubilized in non-reducing SDS sample buffer.

Lane 1: Breast tumour tissue probed with biotinylated antibody purified from ASC-cultures.

Lane 2: Breast tumour tissue probed with biotinylated antibody purified from control serum.

Lane 3: Normal breast tissue probed with biotinylated antibody purified from ASC-cultures.

Lane 4: Normal breast tissue probed with biotinylated antibody purified from control serum.

All tissues and the ASC-probe were obtained from the same patient.

Figure 4:
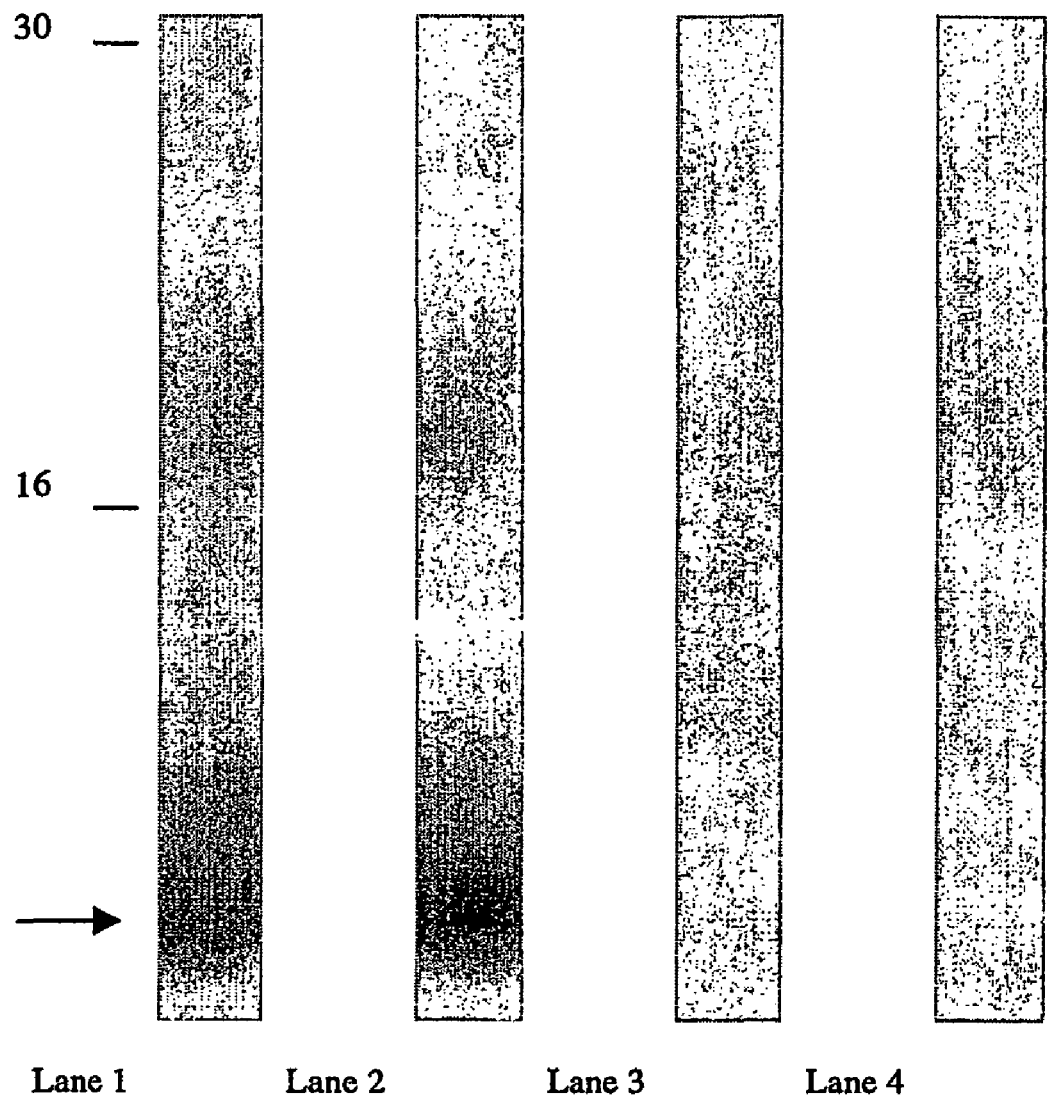

FIG. 4 shows results obtained using samples of urine from breast cancer patients. Samples were subjected to Western blotting on nitrocellulose from a 10% SDS-PAGE gel. Samples were solubilized in non-reducing SDS sample buffer. All strips were probed with ASC culture supernatant.

Lane 1: Urine from breast cancer-positive patient 1
Lane 2: Urine from breast cancer-positive patient 2
Lane 3: Urine from breast cancer-negative patient 1
Lane 4: Urine from breast cancer-negative patient 2.

Figure 5:
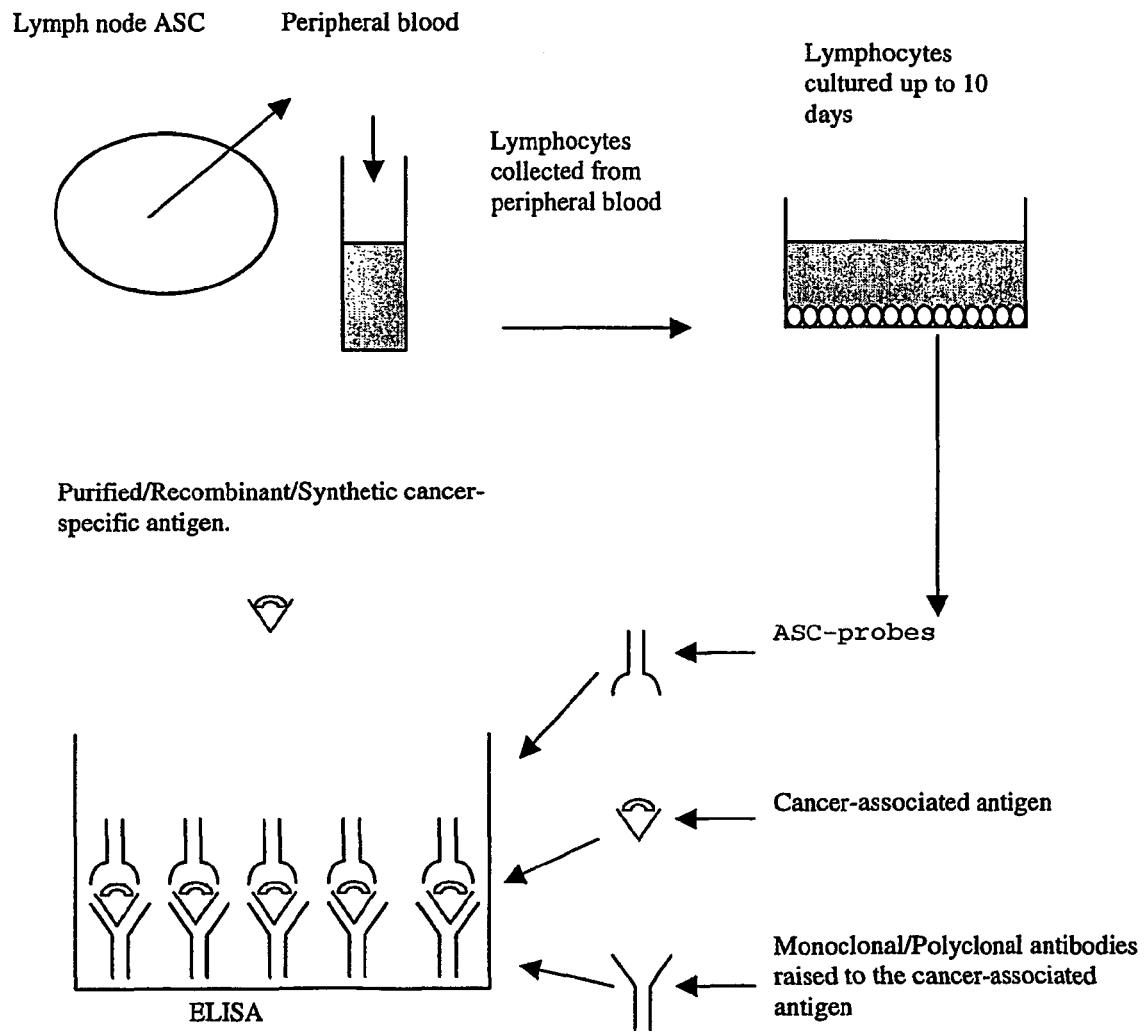

FIG. 5 is a schematic representation illustrating the evaluation of peripheral blood ASC-probes for cancer diagnosis.

Figure 6:
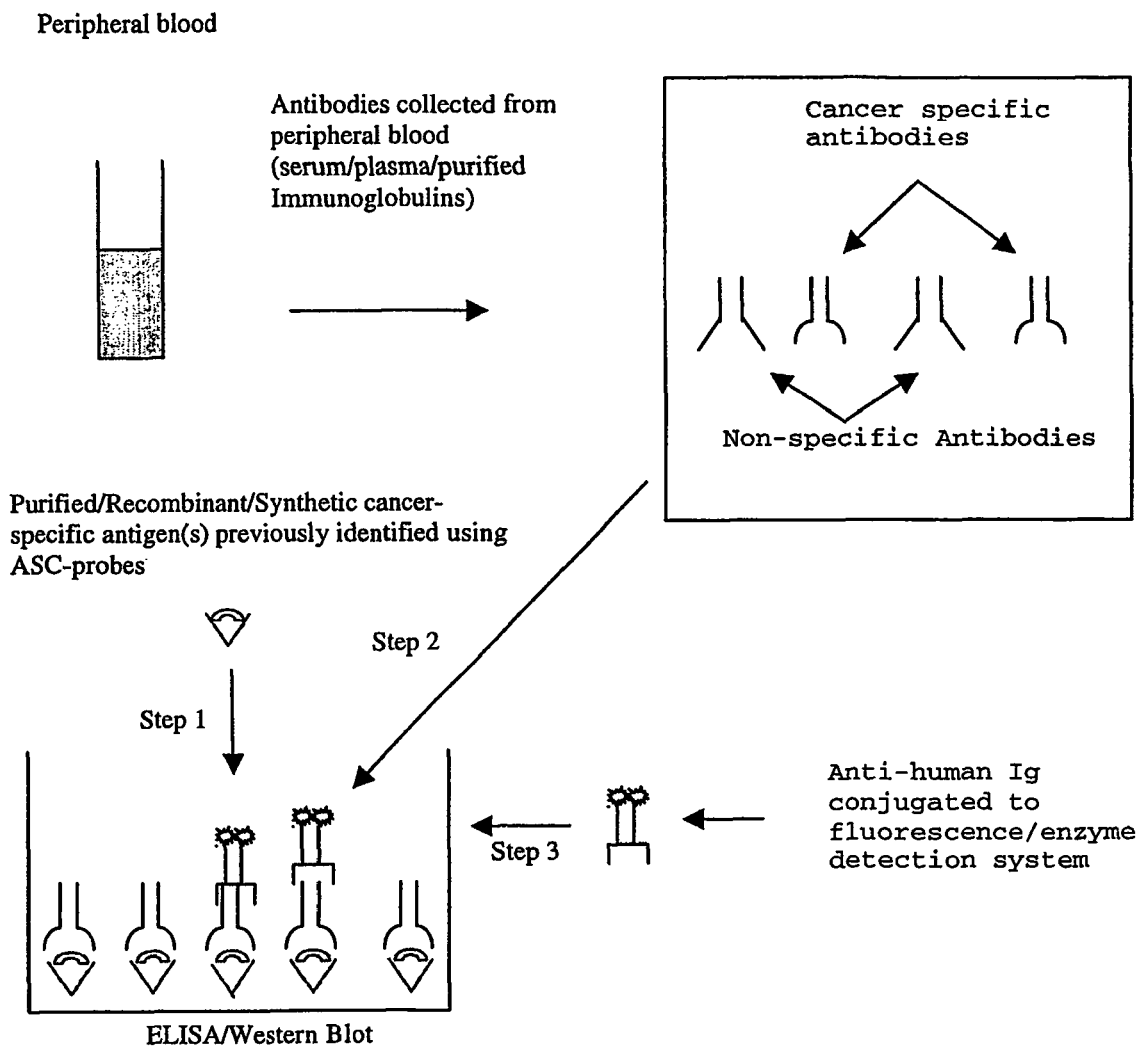

FIG. 6 is a schematic representation illustrating the diagnostic evaluation of peripheral blood and urine for cancer-specific antibodies.

Figure 7:
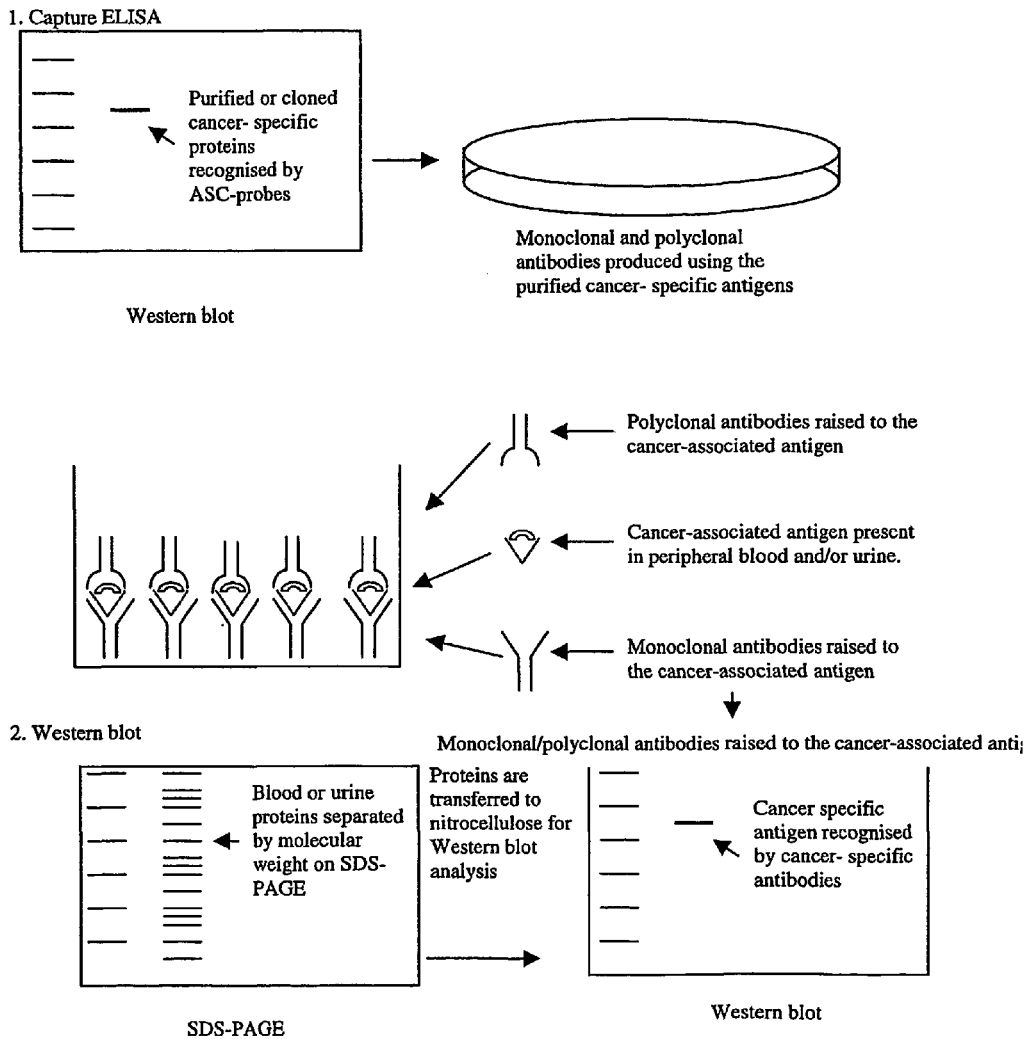

FIG. 7 is a schematic representation illustrating the diagnostic evaluation of peripheral blood and urine for ASC-probe positive antigens.

Figure 8:
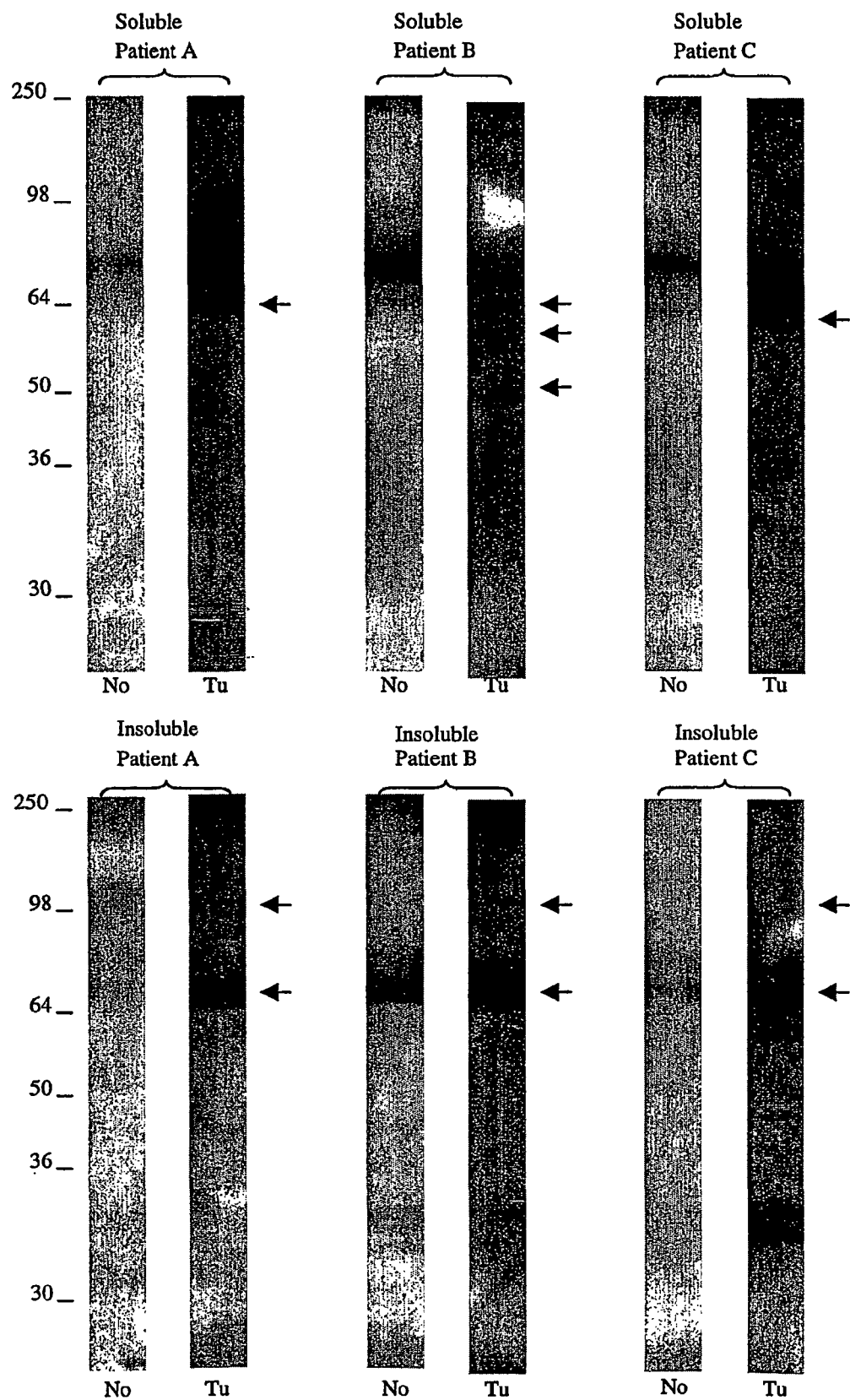

FIG. 8 shows the result of Western blot analysis of normal breast tissue and breast tumour tissue probed with biotinylated antibody obtained from breast-draining lymph nodes. No: Normal tissue; Tu: tumour tissue. Molecular weight standards: 250,000; 98,000; 64,000; 50,000; 36,000; 30,000. The arrows indicate regions of difference between samples from normal and tumour tissue.

Figure 9:
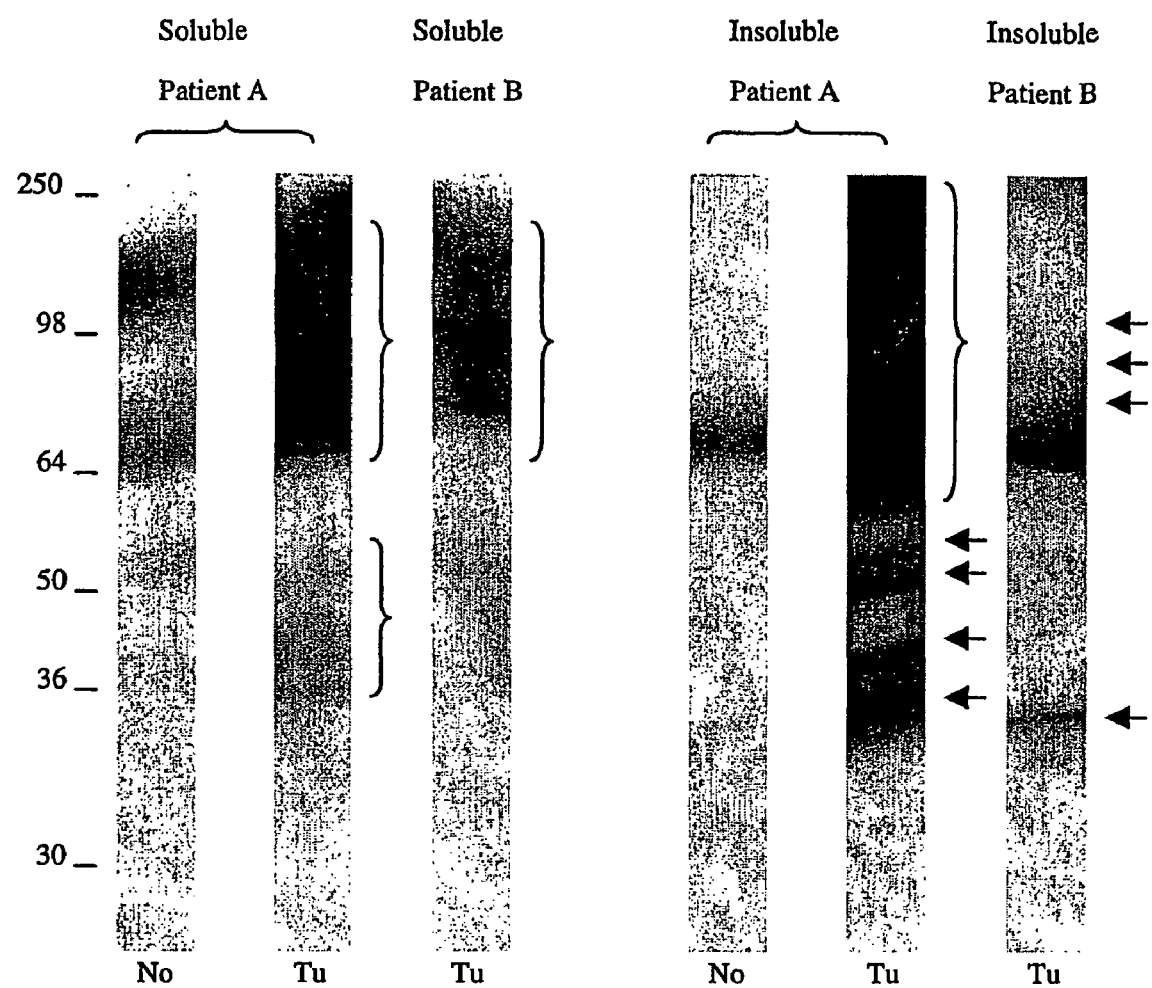

FIG. 9 shows the results of Western blot analysis of normal ovarian tissue and ovarian tumour tissue. No: Normal tissue; Tu: tumour tissue. Molecular weight standards: 250,000; 98,000; 64,000; 50,000; 36,000; 30,000. The arrows and brackets indicate regions of difference between normal tissue and tumour tissue.

Figure 10:
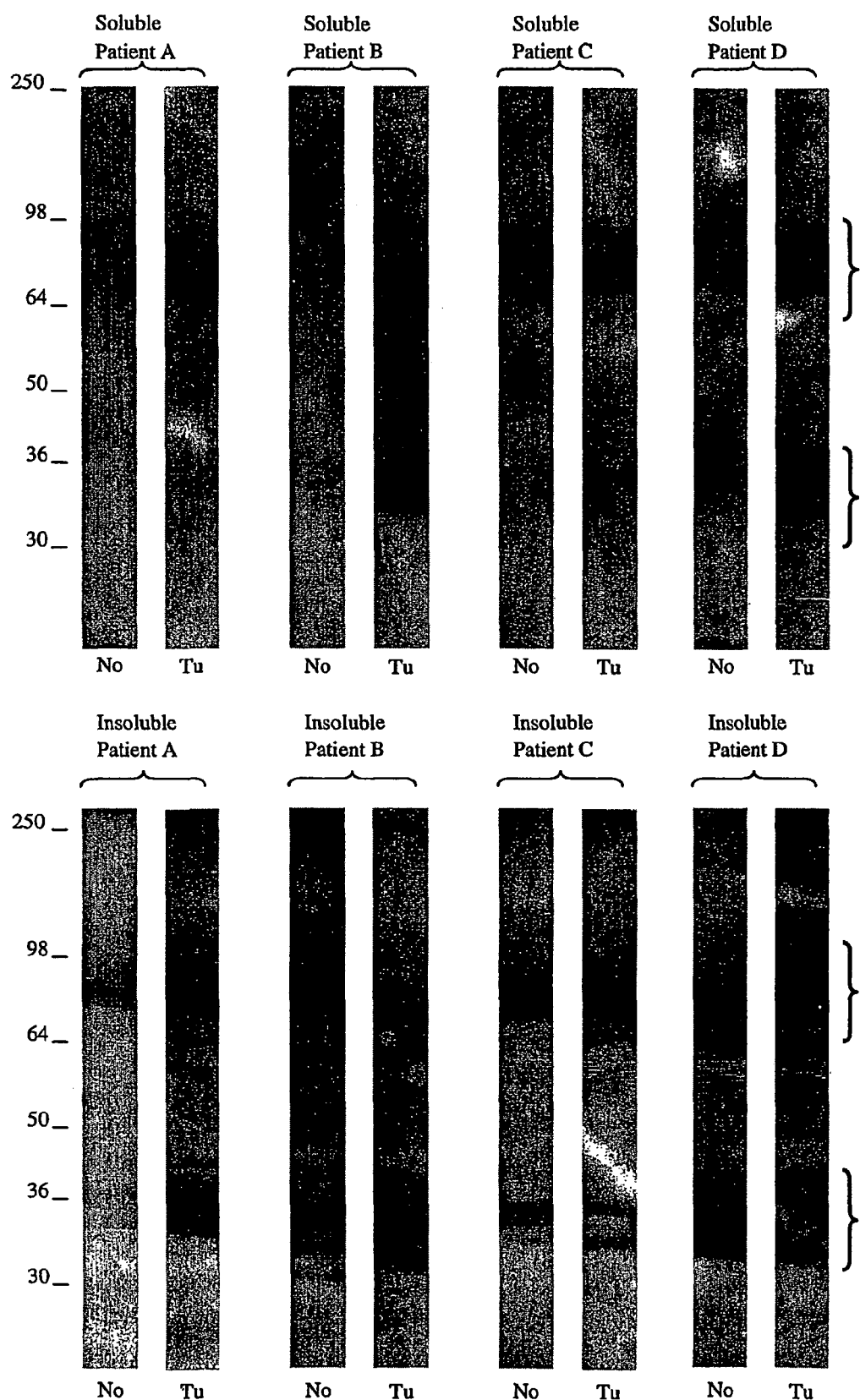

FIG. 10 shows the results of Western blot analysis of normal prostate tissue and prostate tumour tissue probed with biotinylated antibody obtained from prostate-draining lymph nodes of patient A. No: Normal tissue; Tu: tumour tissue. Molecular weight standards: 250,000; 98,000; 64,000; 50,000; 36,000; 30,000. The brackets indicate the regions of difference between the normal tissue and the tumour tissue.

Figure 11:
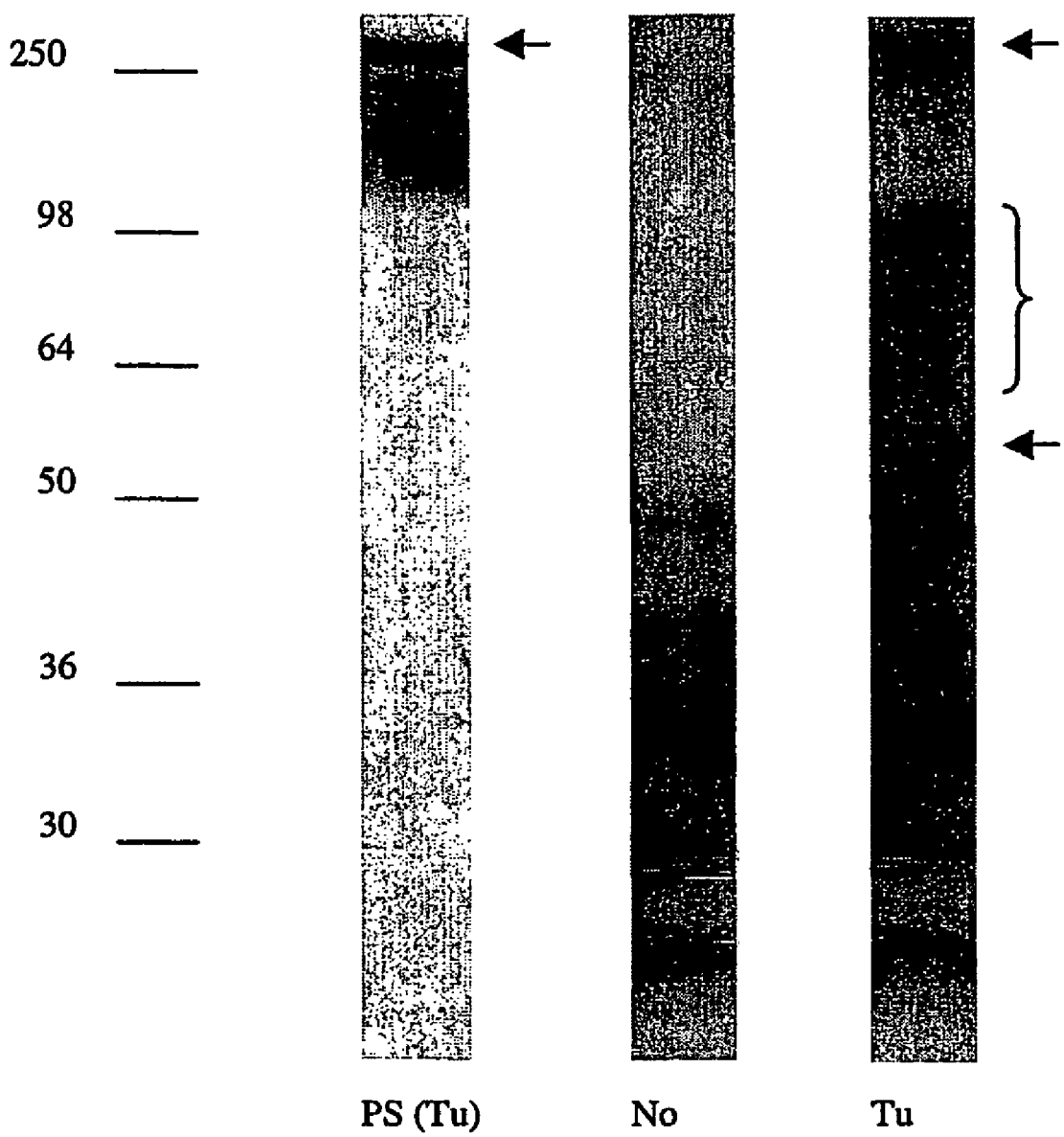

FIG. 11 shows the results of protein staining and Western blot analysis of immunoprecipitated normal ovarian tissue and ovarian tumour tissue probed with biotinylated antibody obtained from ASC-probes generated from the draining lymph nodes of the same patient. PS: Coomassie Blue staining. No: Normal tissue; Tu: tumour tissue. Molecular weight standards: 250,000; 98,000; 64,000; 50,000; 36,000; 30,000. The arrows and brackets indicate regions of difference between normal tissue and tumour tissue.

Figure 12:
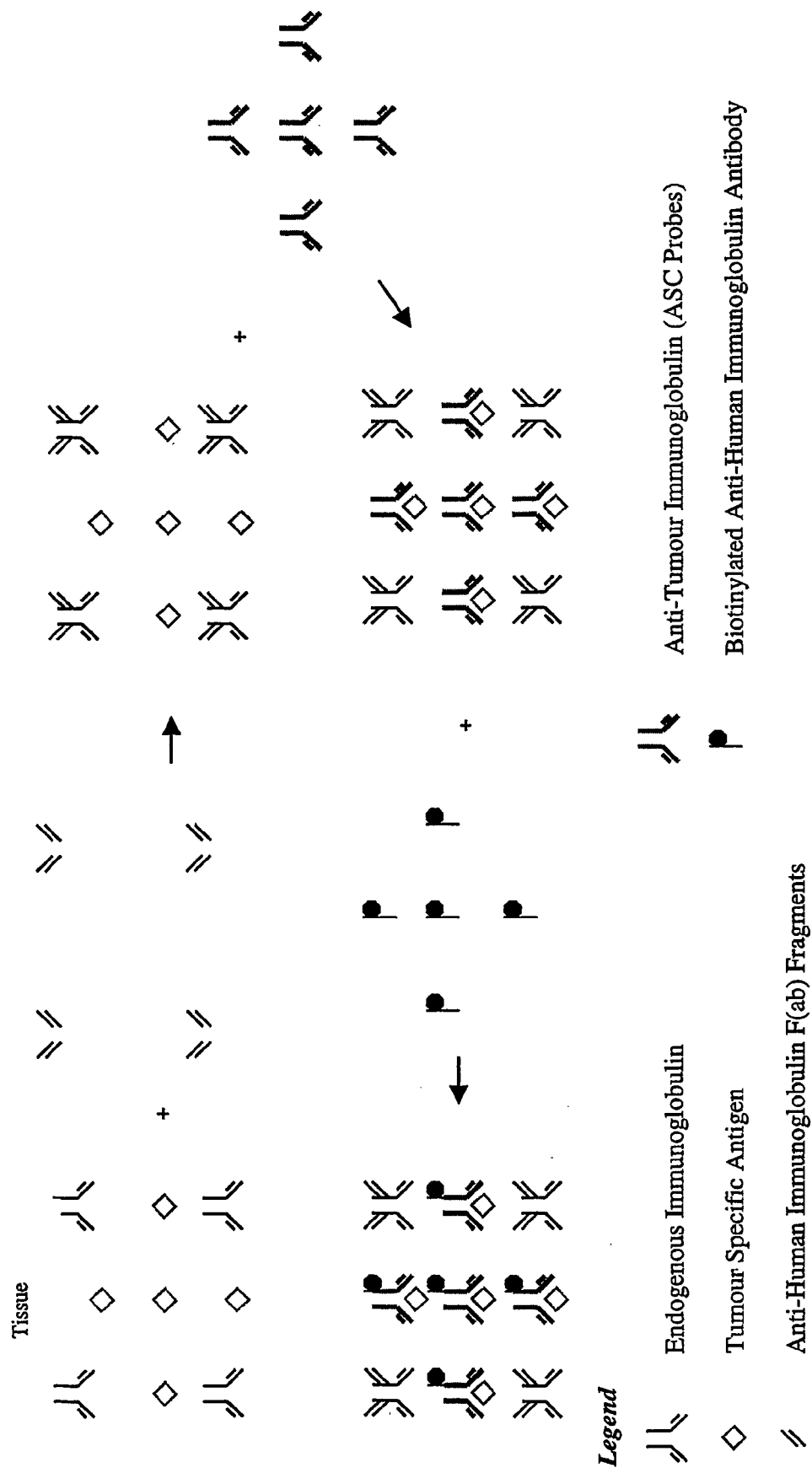

FIG. 12 is a schematic illustration showing how background caused by endogenous IgG in the tissue may be blocked by pre-incubation with monomeric anti-IgG F(ab).

Figure 13:
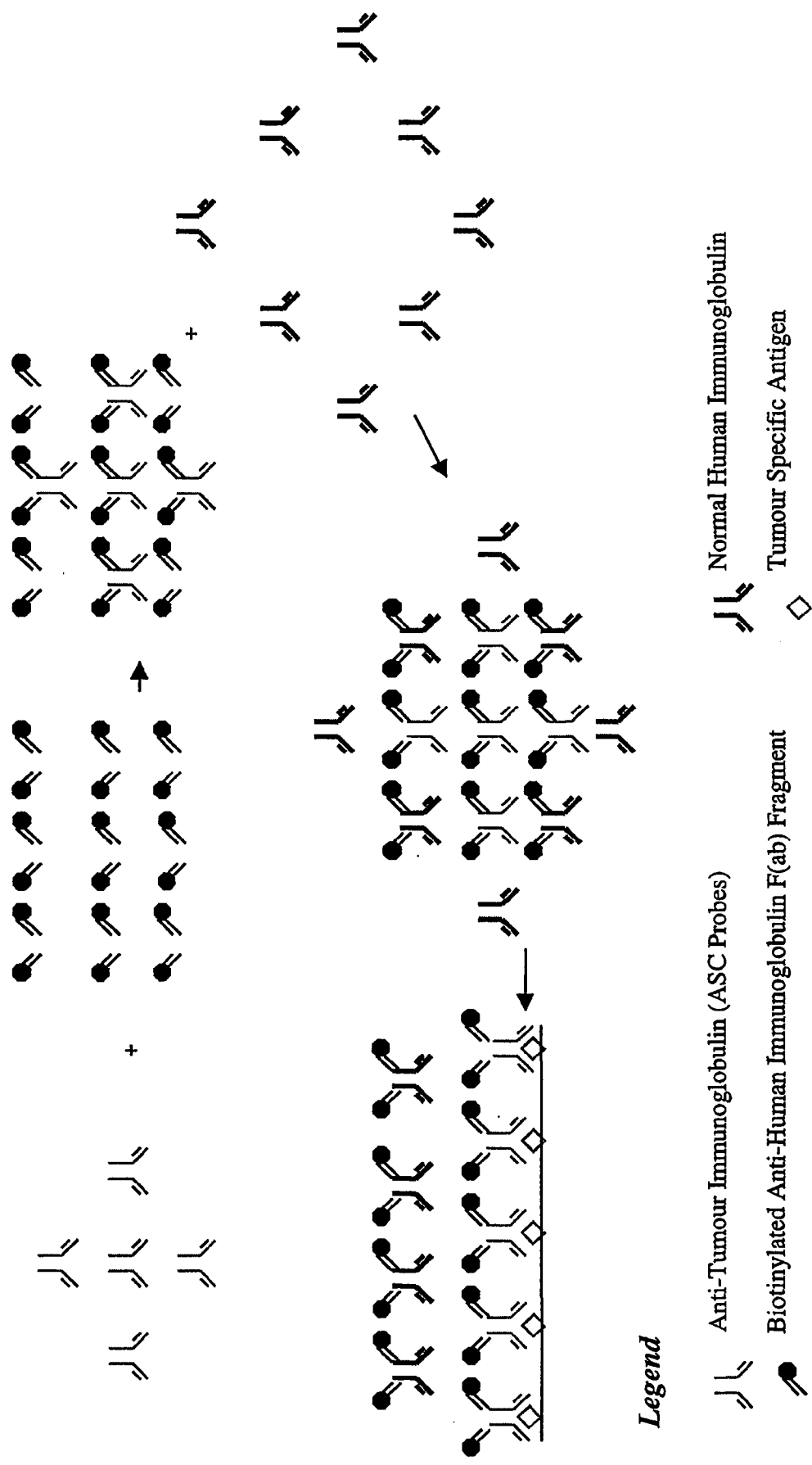

FIG. 13 is a schematic illustration showing how background caused by endogenous IgG can be suppressed by pre-incubation of ASC antibody with excess biotinylated F(ab) fragments of anti-IgG, followed by excess normal IgG.

DETAILED DESCRIPTION OF THE INVENTION

The invention will now be described in detail by way of reference only to the following non-limiting examples and to the drawings.

Monoclonal antibodies directed toward the cancer-specific antigen of the invention are produced using any method which provides for the production of antibody molecules by continuous cell lines in culture. The word "monoclonal" indicates the character of the antibody as being obtained from a substantially homogeneous population of antibodies, and is not to be construed as requiring production of the antibody by any particular method. Examples of suitable methods for preparing monoclonal antibodies include the original hybridoma method of Kohler, et al., 1975, and the human B-cell hybridoma method, Kozbor 1984; Brodeur et al., 1987.

The monoclonal antibodies of the invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., U.S. Pat. No. 4,816,567; Morrison, et al., 1984).

In a preferred embodiment, the chimeric antibody is a "humanized" antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain.

Humanization can be performed following methods known in the art (Jones, et al., 1986; Riechmann, et al., 1988; Verhoeyen, et al. 1988), by substituting rodent complementarity-determining regions (CDRs) for the corresponding regions of a human antibody. Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, for example, Jakobovits, et al., 1993; Jakobovits, et al., 1993; Bruggermann, et al. 1993. Human antibodies can also be produced in phage-display libraries (Hoogenboom, et al., 1991; Marks, et al., 1991).

For diagnostic applications, the antibodies typically will be labeled with a detectable moiety. The detectable moiety can be any one which is capable of producing, either directly or indirectly, a detectable signal. For example, the detectable moiety may be a radioisotope, such as $^3H$, $^{14}C$ $^{32}P$, $^{35}S$, or $^{125}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$, or an enzyme, such as, alkaline phosphatase, betagalactosidase or horseradish peroxidase.

Any method known in the art for separately conjugating the antibody to the detectable moiety may be employed, including those methods described by David et al., 1974; Pain et al., 1981; and Bayer et al. 1990.

The antibodies may be employed in any known assay method, such as competitive binding assays, direct and indirect sandwich assays, and immunoprecipitation assays (Zola, 1987).

Competitive binding assays rely on the ability of a labeled standard (e.g., the cancer-specific antigen or an immunologically reactive portion thereof) to compete with the test sample analyte (the cancer-specific antigen) for binding with a limited amount of antibody. The amount of cancer-specific antigen in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See for example David, et al., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Methods for preparation of divalent and trivalent scFc-type constructs are respectively described in PCT/AU93/00491 and PCT/AU98/00212 by Commonwealth Scientific and Industrial Research Organisation.

Collection of Human Tissue and Cells

Lymphocytes were isolated primarily from lymph nodes, biopsies, peripheral blood and resected cancerous tissue removed during surgery of patients. Samples of tissue from tumours at different stages of growth were obtained from patients after surgery, and classified according to pathological evaluation.

Normal breast and breast cancer tissue were collected from patients undergoing both radical and partial mastectomies. These samples were placed in 4 times SDS sample buffer and stored at −20° C. in preparation for analysis by SDS-PAGE and Western Blotting.

Peripheral blood lymphocytes were obtained during normal serological testing of patients with suspected primary tumours, and during follow-up for the detection of secondary tumours after treatment.

Collection of Urine

Urine samples were collected from patients diagnosed with breast cancer and also patients found after investigation not to have cancer. The urine samples were stored at −20° C. until required. The samples were used in SDS-PAGE without dilution.

Preparation of ASC-Probes

Single cell suspensions were prepared from all available lymph nodes, using standard techniques. Cells were cultured in 2 ml Costar wells or 10 ml Falcon flasks under standard culture conditions for up to 10 days. Cell culture supernatants, designated ASC-probes, were harvested after centrifugation to remove lymphocytes, and stored at −20° C. until used.

Detection of Cancer-Associated Antigens Using ASC-Probes

Lymphocytes were isolated from lymph nodes draining the breast removed during surgery being carried out on patients with breast cancer. Tumours at different stages of growth were also obtained from these patients, and classified according to normal pathological criteria. Normal breast tissue was also obtained.

Figure 1:
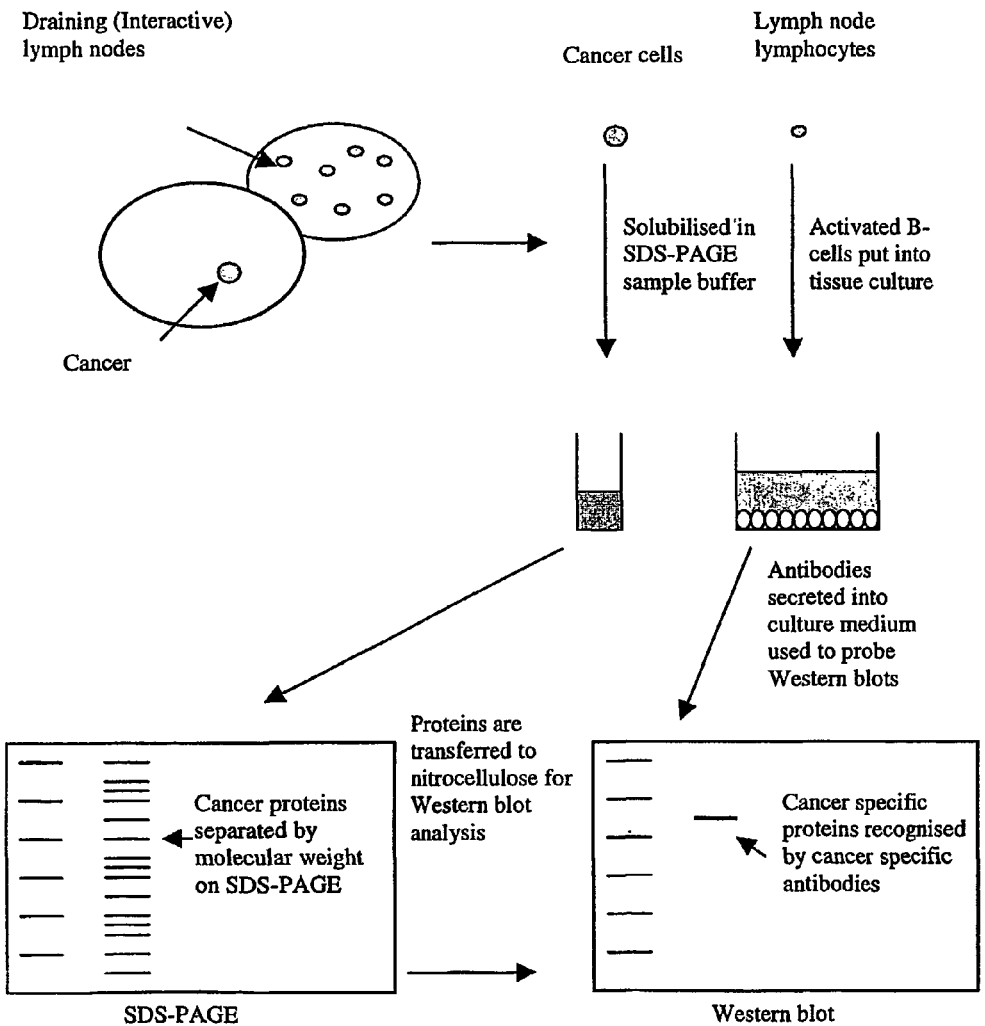
FIG. 1 is a schematic diagram illustrating the use of ASC probes for detection of cancer-associated antigens.

Initial studies on antigen identification were conducted using a conventional Western blotting technique. Normal and cancerous tissues were solubilized in SDS-sample buffer and proteins separated on one-dimensional SDS-PAGE. Following electrophoretic transfer to nitrocellulose membranes (Western blotting), the blots were incubated with IgG, which had been purified from ASC-probes and biotinylated. Control IgG which was purified from human serum and biotinylated was also used to probe similar blots. Bound antibodies were detected after reaction with peroxidase-conjugated streptavidin and diaminobenzidine development or enhanced chemiluminescence (ECL). The method is illustrated schematically in FIG. 1.

The relationship between ASC-probe positive bands and known cancer-associated antigens was examined by stripping the blots of the bound antibodies using standard procedures, and re-probing with monoclonal antibodies directed against various known cancer-associated proteins. SDS-PAGE gels were stained for proteins using the Coomassie blue and silver staining techniques.

Additional studies include surface staining of tumour cells, membrane preparations and immunoprecipitation.

EXAMPLE 1

Preparation of ASC-Culture Supernatants

Lymph nodes draining the breast were collected after surgery and were teased gently in Dulbecco-modified Eagle's medium (DME) containing 10% heat-inactivated fetal calf serum (FCS) and antibiotics (400U/ml penicillin and 0.1 mg/ml streptomycin). Cells were collected, washed three times and resuspended to a final concentration of $5 \times 10^6$ cells/ml in complete culture medium (DME supplemented with 400U/ml penicillin, 0.1 mg/ml streptomycin, 10% FCS, 2 mM glutamine). Pokeweed mitogen (Sigma Aldrich) was added at a concentration of 2.5 µg/ml to increase antibody secretion. Culture flasks containing 10 ml cell suspensions or 24-well culture plates containing 2 ml cell suspension per well were incubated at 37° C. in an atmosphere of 5% $CO_2$ in air, and cell supernatants harvested 5-6 days later. Culture supernatants containing antibodies secreted by antibody-secreting cells (ASC) present in the lymph node cell suspensions were subsequently stored at −20° C. until required.

EXAMPLE 2

Purification and Labelling of Antibodies from Cell Supernatants

Antibodies secreted by the ASC in culture supernatant were purified by affinity chromatography using a Protein-G column (Pharmacia HiTrap Affinity Column, 1 ml). The column was pre-equilibrated with loading buffer (20 mM sodium phosphate, pH 7.0). The cell supernatants were applied to the Protein G column, and the unbound proteins removed using 10 column volumes of loading buffer. Bound proteins were eluted from the column using 3 column volumes of elution buffer (0.1 M glycine/hydrochloric acid, pH 2.7). The eluate was neutralised using 100 µl 5 M tris/hydrochloric acid, pH 8.0. The purified antibody solution was dialysed extensively against phosphate buffered saline (PBS) before being stored at 4° C.

Control antibodies were purified from the serum of a patient who was found not to have breast cancer. The method of purification was identical to that used for the ASC supernatants.

Biotinylation of Purified Antibodies

Purified antibodies (Ab) were incubated with a 0.45 mg/ml (final concentration) of biotin succinimide ester (Biocap NHS Reagent, Calbiochem, California) in DMSO for 2 hours at room temperature. The reaction was stopped by overnight dialysis against PBS. Biotinylated antibodies were then stored at 4° C. until required.

EXAMPLE 3

Western Blotting

Appropriate dilutions of the antigens were loaded on a 10% SDS-PAGE gel and blotted on to nitrocellulose membrane (MSI, Melbourne, Australia). Western blot transfers were performed using the wet transfer apparatus (Bio-Rad Laboratories) at a constant voltage of 100V for 1 hour in transfer buffer (25 mM Tris-HCl pH 8.3, 192 mM glycine and 15% (v/v) methanol). After electrophoretic transfer, the membranes were placed in a blocking solution of 3% skim milk powder in PBS for 1 hour, then washed 3 times with 0.05% Tween 20 in PBS before being probed with antibody. For urine samples, Western blots were probed for 2 hours with undiluted ASC supernatant, followed by incubation for 1 hour with peroxidase-conjugated rabbit anti-human IgG serum (DAKO) at a 1:2000 dilution.

Figure 2:
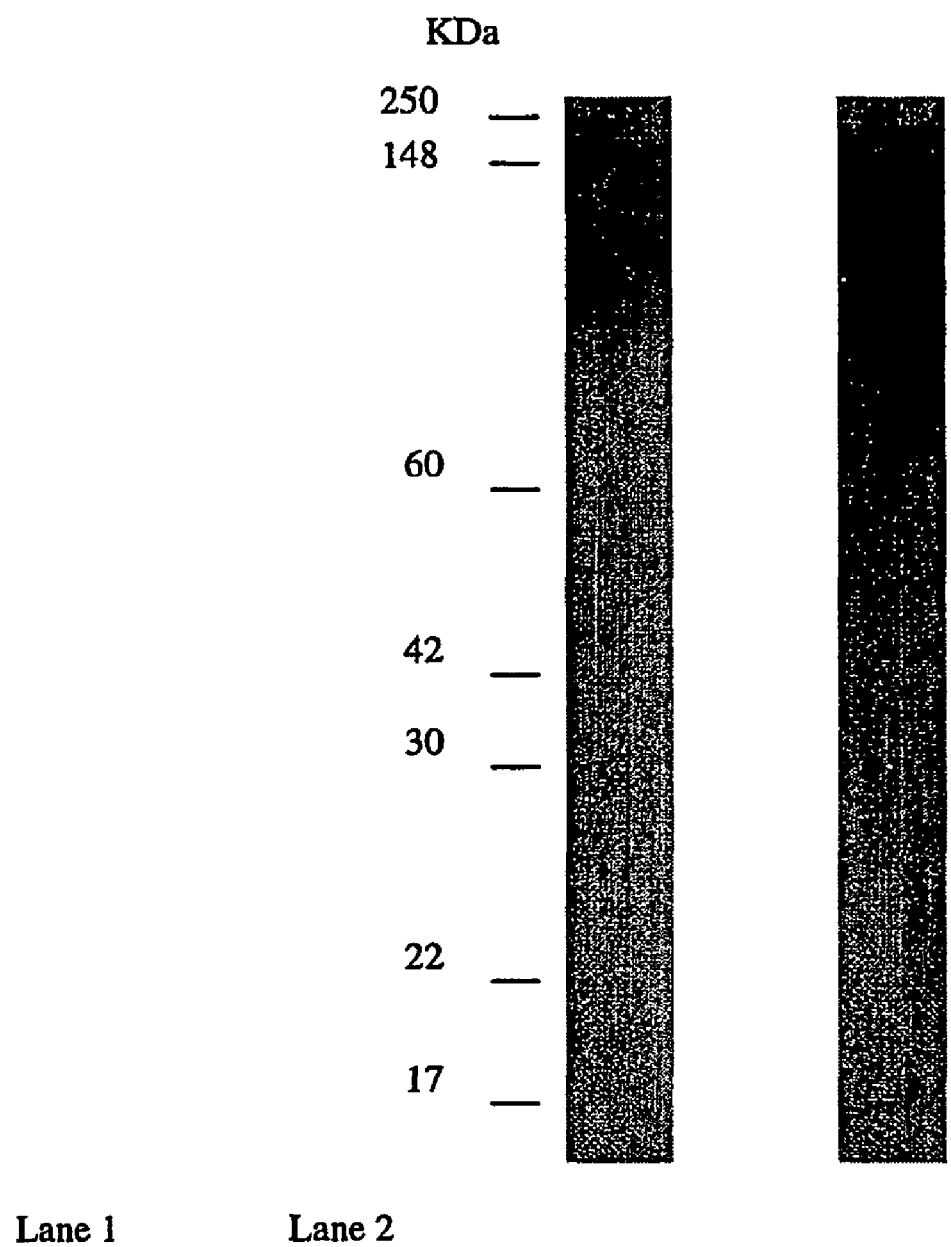
FIG. 2 shows the comparative levels of protein G-purified, biotinylated antibody isolated from ASC culture supernatant from breast lymph node cell cultures. This antibody was used for probing the Western blots in FIGS. 3 and 4. Purified antibody from culture supernatant is shown in lane 1, and antibody purified from control serum is shown in lane 2.

Western blots of breast tissue gave high reactions with the conjugate, due to contamination of the tissue with serum immunoglobulins. A one-step 2 hour incubation with purified biotinylated antibodies was therefore used for these tissues, followed by a 1 hour incubation with peroxidase-conjugated streptavidin (Santa Cruz, USA). All incubations were at room temperature, and all washes were in 0.05% Tween 20 in PBS. Biotinylated antibodies were diluted in 0.5% Tween 20 in PBS containing a dilution of 1 in 50 of non-specific human IgG. Biotinylated cancer-specific antibodies were used at 1 in 150 dilution, and biotinylated control antibodies were used at a 1 in 500 dilution. These dilutions yielded comparable levels of detection by ECL after western blotting and reaction with peroxidase-conjugated streptavidin, as shown in FIG. 2.

After reaction with peroxidase conjugates, the membranes were washed again and then incubated for 1 min in ECL reagent (Amersham Pharmacia Biotech, Sweden) for breast tissue Western blots. Western blots from urine samples were developed with 3,3'-diaminobenzidine tetrahydrochloride (0.5 mg/ml) (DAB, Sigma Aldrich Pty. Ltd., Australia) in citrate buffer (pH 5.0, 10 mM) to which 0.02% (v/v) hydrogen peroxide ($H_2O_2$) had been added. When bands were clearly visible the reaction was stopped with several washes of distilled water.

As shown in FIG. 3, consistently higher background reactivity was observed on Western blots of cancer tissues compared to control breast tissue (lane 2 versus lane 4), although both tissues showed similar protein loading. On Western blots of cancer tissue, several antigens or antigenic regions were clearly reactive with the specific antibody purified from ASC culture supernatants (lane 1) which were not recognized by control antibody (lane 2) and were not present in normal tissue (lane 3). The tumour antigens detected in breast tumour tissue had molecular weights of between approximately 20 and 25 kDa and 40 and 60 kDa (arrows).

Urine Antigens

A low molecular weight antigen was recognized by ASC culture supernatant in each of 2 urine samples from breast cancer patients, as shown in FIG. 3, lanes 1 and 2. This antigen was not detected in any of the 5 control urine samples examined (eg lanes 3 and 4).

EXAMPLE 4

Characterisation and Purification of Cancer-Associated Antigens

The cancer-associated antigen identified using ASC-probes are fractionated and purified using conventional analytical and biochemical techniques, such as high performance electrophoretic chromatography, capillary electrophoresis, antibody affinity chromatography, immunoprecipitation and high performance liquid chromatography. Once purified, the biochemical and biophysical characteristics of the antigens are determined, using standard techniques, including amino acid sequencing. Once sufficient sequence information is obtained, the gene encoding the antigen can be isolated using methods well known in the art, and used to produce recombinant antigen. Alternatively the amino acid sequence information can be used to make synthetic antigen or fragments thereof, using well-known solid phase synthesis methods. If the antigen is non-protein in nature, for example a carbohydrate structure, other methods of synthesis known in the art may be used. For example, solid phase and solution phase synthesis for oligosaccharides have been described by Alchemia Pty Ltd (PCT/AU01/00054; PCT/AU98/00131; PCT/AU98/00808; PCT/AU01/00028).

The purified, synthetic or recombinant antigen(s) can be used in classical diagnostic assays, such as ELISA assays, to detect antibodies in the serum of patients, as shown in FIG. 5.

EXAMPLE 5

Evaluation of Peripheral Blood ASC-Probes for Cancer Diagnosis

Once cancer-associated antigens have been identified using ASC-probes and purified, cloned, or synthesised, they are used to detect circulating ASCs in peripheral blood of patients at different stages of disease, using methods such as ELISA and Western blotting. This is illustrated schematically in FIG. 6. The results are compared to those obtained using standard tumour detection methods and serum antibody responses. In addition, investigations are initiated to detect the early appearance of specific ASCs in peripheral blood of high-risk patients who are undergoing regular follow-up checks for tumour re-appearance after primary therapy.

EXAMPLE 6

Diagnostic Evaluation of Peripheral Blood and Urine for ASC-Probe Positive Antigens Once cancer-associated antigens have been identified using ASC-probes, the purified, cloned or synthesised antigens are used to develop both polyclonal, monoclonal and/or synthetic antibodies. The specific antibodies are used to detect circulating cancer-associated antigen in peripheral blood of patients at different stages of disease, using methods such as ELISA and Western blotting. The specific antibodies are also investigated in a similar manner for use in detecting cancer-associated antigens in the urine of patients at various stages of disease, which would enable a non-intrusive diagnostic test. This is illustrated schematically in FIG. 7.

EXAMPLE 7

Soluble and Insoluble Fractions from Breast Tissue

Soluble and insoluble fractions were generated from normal breast tissue and breast tumour tissue by five cycles of freeze-thawing in 20 mM Tris-HCl, pH8.0. The samples were centrifuged to pellet the insoluble components, followed by analysis of each fraction using 10% SDS-polyacrylamide gel electrophoresis under non-reducing conditions. Following Western blot transfer, the samples were analysed using biotinylated IgG purified from ASC probes generated from breast tumour tissue as described in examples 1 and 2. Samples from three individual patients, designated Patients A-C, were analysed.

As shown in FIG. 8, soluble and insoluble fractions probed with biotinylated ASC immunoglobulins revealed several regions of activity in both the normal and tumour tissue. Results from the patient whose tissue was used to generate the ASC probe are not shown, because normal breast tissue could not be obtained from this patient.

Various differences between the normal and tumour tissue in both the soluble and insoluble fractions were identified. In the soluble fraction, a region at approximately 70 kDa is reactive in both the normal and the tumour tissue. The major difference between tumour tissue and normal tissue is seen at approximately 64 kDa, with strong reactivity in the tumour tissue but not in the normal tissue. In the insoluble fraction the differences are not as prominent: however, the tumour samples appear to have a region of activity above 98 kDa which does not appear in the normal tissue.

EXAMPLE 8

Soluble and Insoluble Fractions From Ovarian Tissue

Soluble and insoluble fractions were prepared from normal ovarian tissue and ovarian tumour tissue, and analysed by Western blotting as described in Example 7. Samples from two individual patients, designated Patient A and Patient B respectively, were analysed. ASC-probes generated from Patient A were used.

As shown in FIG. 9, Western blots of the soluble fraction of normal tissue from Patient A detect two main reactive areas, at approximately 70 and 120 kDa. In the soluble fraction of tumour tissue of the same patient, additional strong bands were identified between 70 and 150 kDa, with weaker reactivity being detected between 36 and 50 kDa. In the soluble fraction from Patient B (tumour, lane 3), the same regions of reactivity were seen, but the bands were less intense. The insoluble fraction from normal tissue showed one area of reactivity at approximately 70 kDa. The insoluble fraction from tumour tissue of Patient A showed strong reactivity above 60 kDa, as well as bands of reactivity at approximately 36 and 50 kDa. The insoluble fraction of the tumour tissue from Patient B showed strong reactivity at approximately 70 kDa and 36 kDa.

EXAMPLE 9

Soluble and Insoluble Fractions from Prostate Tissue

Soluble and insoluble fractions were prepared from normal prostate and prostate tumour tissue and analysed by Western blotting as described in Example 8. Samples from four individual patients, designated Patients A-D, were analysed. ASC-probes generated from Patient A were used.

As shown in FIG. 10, soluble and insoluble fractions probed with biotinylated ASC immunoglobulins revealed several regions of reactivity in both the normal and the tumour tissues. It should be borne in mind that tumour tissue will usually include significant amounts of normal tissue, whereas normal tissue would be expected to include very few or no tumour cells. However, there may be some tumour cells in the normal sample, particularly in the case of prostate cancer, because the hyperplastic nature of the whole prostate at the time of collection generally makes it difficult to distinguish the true normal tissue from the hyperplastic tissue and borderline tumour tissue. Accordingly, bands which are present in the tumour tissue but not in the normal tissue are considered to be potential tumour antigens.

Various differences between the normal and tumour tissue were identified in both the soluble and insoluble fractions, as indicated by the brackets. Two main reactive areas were seen in the normal and tumour samples in both the soluble and insoluble fractions, at approximately 30 to 40 kDa and 60 to 100 kDa. In the soluble fraction, all the tumour tissue showed strong bands between 60 and 100 kDa, with weaker reactivity being detected between 30 and 40 kDa. In the insoluble fraction, all the tumour tissue examined showed strong bands between 60 and 100 kDa with the exception of Patient B. Strong reactivity was also detected between 30 and 40 kDa in the insoluble fraction of the tumour samples.

EXAMPLE 10

Immunoprecipitation of Tumour Specific Antigens

If the body is capable of producing specific antibodies to tumour-specific antigens, then these antibodies should be present in the tumour itself, and should form complexes with these antigens. We thought that it might be possible to use these antibodies to collect tumour-specific antigens by immunoprecipitation.

Soluble fractions were extracted from both normal ovarian tissue and ovarian tumour tissue by five cycles of repeated freezing and thawing of the tissue in 20 mM Tris-HCL, pH8.0. Immune complexes were then extracted from the soluble fractions using Protein A-Sepharose beads (Pharmacia). The soluble fractions were mixed with Protein A-Sepharose, and allowed to bind for 3 hours at room temperature, with constant mixing. The Protein A-Sepharose beads were washed extensively with 20 mM Tris-HCL pH8.0 before elution of the complexes with elution buffer (0.1 M Glycine-HCl, pH2.5). The eluate was neutralised using 100 µl 5 mM Tris-HCl pH8.0.

Eluates were subjected to Western blotting as described in Example 7. Following Western blot transfer, the examples were analysed using biotinylated IgG purified from ASC probes generated from the same patient.

As shown in FIG. 11, protein staining with Coomassie Blue revealed immunoglobulin purified from tumour samples using Protein A-Sepharose. A band of higher molecular weight (indicated by an arrow in sample PS(Tu)) was also detected; this possibly indicated some of the immune complexes. On Western blots of normal tissue immunoprecipitate, several reactive bands were seen at molecular weights below 50 kDa. However, in the tumour tissue immunoprecipitate, additional bands were identified at approximately 250 kDa and 55 kDa, and there was also a region of activity between 98 and 64 kDa. These results indicate that tumour antigens are able to be collected using this method.

EXAMPLE 11

F(ab) Blocking of Endogenous Immunoglobulin

The major difficulty in detecting candidate tumour antigens by Western blot analysis using ASC probes is a consequence of the use of peroxidase-conjugated antibodies against human immunoglobulins for the detection of the antigens. All tissue samples, whether from tumours or from normal tissue, will include significant amounts of blood, and therefore will contain human immunoglobulins such as IgGs, the great majority of which are directed to antigens other than tumour antigens and are therefore irrelevant to the detection of tumour antigens. The presence of this IgG creates a large background of non-specific signals in Western blots.

In addition to the purification and direct biotinylation of antibodies as described above, there are at least two alternative strategies which may be used to overcome this problem. The first utilises a preliminary step of blocking endogenous IgG in the sample with F(ab) fragments.

FIG. 12 illustrates schematically how endogenous IgG from blood in the tissue sample may be "blocked" from detection by incubating the blots with monomeric F(ab) fragments of antihuman IgG (Nielsen et al., 1987; Louis Carl et al., 1993), prior to probing the membrane with peroxide-conjugated anti-human IgG antibodies of the same specificity as that of the F(ab) fragments. In this way, the background may be reduced to manageable levels, thus increasing the chance of detecting specific signals.

EXAMPLE 12

F(ab) Amplification/Detection System

A second strategy for overcoming the problem of lack of specificity utilises the suppression of background signal. FIG. 13 illustrates this method, in which the background caused by endogenous IgG present in blood in the tissue can be suppressed. The ASC antibodies produced in tissue culture are incubated with an excess of biotinylated F(ab) and anti-human IgG, followed by an excess of normal human IgG, so that all biotinylated F(ab) fragments are bound to IgG (Hierck et al., 1994; Fung et al., 1992). These complexes are then used to probe the membrane, following by washing and detection with peroxidase-conjugated streptavidin, which binds to biotin. Since all the F(ab) anti-human IgG is already bound to IgG, whether in the form of ASC antibodies or normal IgG, any IgG already present on the blot will not be detected.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Banchereau, J., F. Bazan, et al. (1994). The CD40 antigen and its ligand. *Annu Rev Immunol* 12: 881-922.

Bayer et al., Meth. Enz. 184:138-163 (1990).

Bowles V M, Brandon M R and Meeusen E. (1995) Characterisation of local antibody responses to the gastrointestinal parasite *Haemonchus contortus. Immunology* 84: 669-674.

Bowles V M, Meeusen ENT, Young A R, Nash A D, Andrews A E & Brandon M R (1996) Vaccination of sheep against larvae of the sheep blowfly (*Lucilia cuprina*). *Vaccine* 14: 1347-1352.

Brodeur et al., Monoclonal Antibody Production Techniques and Applications, pp. 51-63 (Marcel Dekker, Inc., New York, 1987)

Bruggermann, et al., Year in Immuno. 7:33 (1993).

David et al., *Biochemistry* 13:1014-1021 (1974).

Fung, K. M., et al., A novel modification of the avidinbiotin complex method for immunohistochemical studies of transgenic mice with murine monoclonal antibodies. J Histochem Cytochem, 1992. 40(9): p. 1319-28

Goding, J. W. (1986). *Monoclonal Antibodies: Principles and Practice*, London, Academic Press Limited.

Hierck, B. P., et al., Modified indirect immunodetection allows study of murine tissue with mouse monoclonal antibodies. J Histochem Cytochem, 1994. 42(11): p. 1499-502.

Hoogenboom, et al., *J. Mol. Biol.* 227:381 (1991).

Jakobovits, et al., *Proc. Natl. Acad. Sci.* 90: 2551-2555 (1993).

Jakobovits, et al., *Nature* 362:255-258 (1993).

Jehuda-Cohen T, Slade B A, Powell J D, Villinger F, De B, Folks T M, McClure H M, Sell K W, and Anwar-Ansar A (1990) Polyclonal B-cell activation reveals antibodies against human immunodeficiency virus type 1 (HIV-1) in HIV-1 seronegative individuals. *Proc. Natl. Acad. Sci.* 87: 3972-3976.

Jones, et al., *Nature* 321:522-525 (1986).

Kamath, A. T., J. Pooley, et al. (2000). The development, maturation, and turnover rate of mouse spleen dendritic cell populations. *J Immunol* 165(12): 6762-70

Kohler, et al., *Nature* 256:495-497 (1975)

Kozbor, *J. Immunol.* 133:3001 (1984);

Lewis Carl, S. A., I. Gillete-Ferguson, and D. G. Ferguson. An indirect immunofluorescence procedure for staining the same cryosection with two mouse monoclonal primary antibodies. *J. Histochem Cytochem.*, 1993. 41(8): p. 1273-8.

Marks, et al., *J. Mol. Biol.* 222:581 (1991).

Meeusen E, Brandon M R (1994a) Antibody secreting cells as specific probes for antigen identification. *Journal of Immunological Methods* 172: 71-76.

Meeusen E, Brandon M R (1994b) The use of antibody-secreting cell probes to reveal tissue-restricted immune responses during infection. *European Journal of Immunology* 24:469-474.

Meeusen ENT and J F Maddox (1999) Progress and expectations for helminth vaccines. *Advances in Veterinary Medicine* 41: 241-256.

Morrison, et al., *Proc. Natl. Acad. Sci.* 81:6851-6855 (1984)).

Nielsen, B., et al., A method for the blocking of endogenous immunoglobulin on frozen tissue sections in the screening of human hybridoma antibody in culture supernatants. Hybridoma, 1987. 6(1): p. 103-9.

Pain et al., *J. Immunol. Meth.* 40:219-231 (1981).

Riechmann, et al., *Nature*, 332:323-327 (1988).

Verhoeyen, et al., *Science* 239:1534-1536 (1988)

Walker J, Jackson H, Eggleton D, Meeusen E, Brandon M R (1994) Identification of a novel antigen from *Corynebacterium pseudotuberculosis* that protects sheep against caseous lymphadenitis. *Infection and Immunity* 62: 2562-2567.

Walker, J, Lee, R, Mathy, N, Doughty S and Conlon, J (1996) Restricted B cell responses to microbial challenge of the respiratory tract. *Veterinary Immunology and Immunopathology* 54: 197-204.

Ward et al (1989) *Nature* 241: 544-546

Zola. Monoclonal Antibodies: A Manual of Techniques. pp. 147-158 (CRC Press, Inc., 1987).

The invention claimed is:

1. A method for producing an antibody-secreting cell probe (ASC-probe) against a cancer-specific antigen, comprising the steps of:
   (a) obtaining a biological sample from an animal suffering from a cancer;
   (b) isolating a population of cells from the biological sample;
   (c) culturing the cells in vitro in a suitable culture medium, wherein said cells are not subjected to in vitro fusion; and
   (d) harvesting antibodies produced by lymphoid cells present in the cell population to produce an ASC-probe; in which the cancer is a leukemia.

2. A method according to claim 1, in which the biological sample is from a tissue area containing lymphoid cells which is close to the site of the cancer.

3. A method according to claim 1, in which the biological sample is selected from the group consisting of blood, lymph or lymph node, and bone marrow.

4. A method according to claim 3, in which the biological sample is spleen or bone marrow.

5. A method according to claim 1, in which the biological sample is a draining lymph node.

6. A method according to claim 1, in which the biological sample is not blood.

7. A method according to claim 1, in which the cells isolated from the biological sample include B lymphocytes and/or B memory cells.

8. A method according to claim 1, in which the sample is subjected to one or more processes for enrichment of lymphocytes or B lymphocytes, or subjected to one or more processes for selectively depleting cell populations which suppress antibody secretion.

9. A method according to claim 1, in which the antibodies are separated and purified from the culture medium harvested from the cultured cells.

10. A method of isolating an antigen associated with a cancer, comprising the steps of:
    (a) obtaining a tissue or cell sample from a cancer;
    (b) culturing the cells in a suitable medium;
    (c) harvesting antibodies produced by lymphoid cells present in the cell population to produce an ASO-probe;
    (d) reacting a further sample with the ASC-probe produced in (c) to detect at least one antigen associated with a cancer; and
    (e) isolating the antigen detected,
    in which the antigen is associated with a specific stage of development of the cancer.

11. A method according to claim 10, in which proteins present in the tissue or cell sample are separated by electrophoresis, and the separated proteins are optionally transferred to nitro-cellulose, nylon or other sheets.

12. A method according to claim 10, in which in step (d) the product produced by reaction of the further sample with the ASC-probe is detected using a detection assay selected from the group consisting of Western blotting, immunoprecipitation assay, a radioimmunoassay, an enzyme-linked immunoassay, chemiluminescent assay and immunofluorescent assay.

13. A method for purifying a cancer-specific antigen, comprising the steps of:
    (a) isolating a population of cells from the biological sample;
    (b) culturing the cells in vitro in a suitable culture medium;
    (c) harvesting antibodies produced by lymphoid cells present in the cell population to produce an ASC-probe;
    (d) subjecting a crude antigen mixture present in an extract of cancer cells or cancer tissue to affinity chromatography using the ASC-probe prepared in step (c), immobilized on a suitable support; and
    (e) isolating antigen bound to the immobilized ASC-probe;
    in which the antigen is associated with a specific stage of development of the cancer.

* * * * *